United States Patent [19]

McKenzie et al.

[11] Patent Number: 5,075,108
[45] Date of Patent: Dec. 24, 1991

[54] MELPHALAN DERIVATIVES

[75] Inventors: Ian F. C. McKenzie, Brunswick; Geoffrey A. Pietersz, Ringwood; Mark Smyth, Lower Plenty, all of Australia

[73] Assignee: Consolidated Pharmaceuticals, Limited, Queensland, Australia

[21] Appl. No.: 127,663

[22] PCT Filed: Dec. 22, 1986

[86] PCT No.: PCT/AU86/00392

§ 371 Date: Dec. 21, 1987

§ 102(e) Date: Dec. 21, 1987

[87] PCT Pub. No.: WO87/04154

PCT Pub. Date: Jul. 16, 1987

[30] Foreign Application Priority Data

Jan. 3, 1986 [AU] Australia .............................. PH4085

[51] Int. Cl.$^5$ ...................... A61K 39/44; C07K 15/28; C07K 17/00

[52] U.S. Cl. .................................... 424/85.9; 530/388; 530/390; 530/391; 435/174; 514/155; 562/450; 560/41

[58] Field of Search ....................... 530/388, 390, 391; 424/85.91; 435/174; 514/155; 562/450; 560/41

[56] References Cited

U.S. PATENT DOCUMENTS

| | | | |
|---|---|---|---|
| 3,725,470 | 4/1973 | Bretschneider et al. | 562/445 |
| 4,046,722 | 9/1977 | Rowland | 260/6 |
| 4,315,851 | 2/1982 | Yoshikumi et al. | 530/391 |
| 4,401,592 | 8/1983 | Yoshikumi et al. | 424/85.91 |
| 4,543,211 | 9/1985 | Kato et al. | 260/112 B |
| 4,738,843 | 4/1988 | Oguchi et al. | 424/85 |

FOREIGN PATENT DOCUMENTS

| | | | |
|---|---|---|---|
| 0115171 | 8/1984 | European Pat. Off. | 530/391 |
| 1292660 | 4/1969 | Fed. Rep. of Germany . | |
| 1109005 | 1/1956 | France . | |
| 0193437 | 11/1982 | Japan | 562/445 |
| 0671070 | 4/1952 | United Kingdom | 562/445 |
| 1315611 | 5/1973 | United Kingdom | 562/445 |
| 1321161 | 6/1973 | United Kingdom | 562/445 |

OTHER PUBLICATIONS

Blair et al (1983) J. Immunol. Methods 59:129–143.
Chemical Abstract No. 156683d, vol. 82, No. 23 (1975).
Arm. Khim. Zh., vol. 27, No. 11, pp. 997–999(1974) and translation thereof.

Primary Examiner—Jeffrey E. Russel
Assistant Examiner—Kay Kim
Attorney, Agent, or Firm—Finnegan, Henderson, Farabow, Garrett & Dunner

[57] ABSTRACT

A compound of formula I

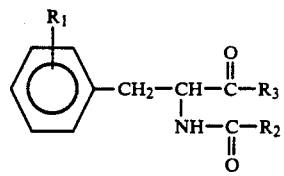

Formula I wherein $R_1$ is of formula II

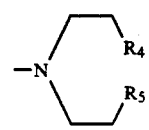

Formula II wherein $R_4$ and $R_5$, which may be the same or different, are bromo, chloro, iodo or alkylsulphonyl;
$R_2$ is of formula III

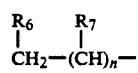

Formula III wherein $R_6$ and $R_7$, which may be the same or different, are H, alkyl, aryl, carboxy, hydroxy or amino and n is 0-10; and
$R_3$ is hydroxy or a group capable of being cleared and replaced by a radical having an antigen binding site or $R_3$ is a radical having an antigen binding site.

16 Claims, 14 Drawing Sheets

MELPHALAN DERIVATIVES

This invention relates to melphalan derivatives. Formulas are set out in the accompanying drawings. The present invention provides a compound of formula I

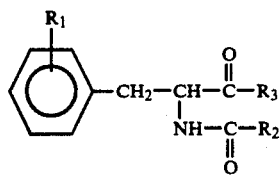

Formula I wherein $R_1$ is of formula II

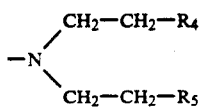

Formula II wherein $R_4$ and $R_5$, which may be the same or different, are bromo, chloro, iodo or alkylsulphonyl; $R_2$ is of formula III

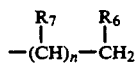

Formula III wherein $R_6$ and $R_7$, which may be the same or different, are H, alkyl, aryl, carboxy, hydroxy or amino and n is 0-10; and
$R_3$ is hydroxy or a group capable of being cleared and replaced by a radical having an antigen binding site or $R_3$ is a radical having an antigen binding site.

Preferred alkyl groups are those containing 6 or less carbon atoms. Preferred aryl groups are those containing 12 or less carbon atoms.

The $R_1$ group may occur in ortho-, meta- or para-position.

Preferred compounds of formula I are those where —$R_3$ is a group capable of being cleared and replaced by a antibody. Such —$R_3$ groups include those which with the adjacent —CO-group are active ester groups. A particular group as $R_3$ is N-hydroxysuccinimide. Other $R_3$ groups include mixed anhydrides, N-hydroxysolphosuccinimides, azides and p-nitrophenyl esters.

It is preferred that $R_3$ is an antibody.

The antibody may be a monoclonal antibody. Antibodies useful in the present invention included those showing specificity for breast, brain, melanoma, lung, pancreas and colon tumours.

The antibody may be an intact immunogobulin or a fragment of an immunogobulin maintaining a sufficiency of an antigen binding site such that it is preferentially absorbed by a tumour cell as compared to a non tumour cell.

Thus, in addition to whole antibodies, it is also possible to utilize F(ab')$_2$ and F(ab') fragments.

Still further antibody polymers such as antibody pentamers IgM and derivatives of these such as immunogobulin monomers may be used.

Also usable are $IgC_{2a}$, $IgG_{2b}$, $IgG_1$, and $IgG_3$.

The compounds of formula I, II and III may be coupled indirectly to monoclonal antibodies via an inert carrier molecule such as human serum albumin or synthetic polymers.

The compounds of this invention may be combined with pharmaceutically acceptable carriers.

The mode of administration of the compounds of this invention will be as selected. In particular, the compounds of this invention may be administered intravenously, intraperitonealy, intrapleuraly, intrapericardialy, and intracerebo spinal fluid.

Compounds in accordance with the present invention can be prepared by acylating a starting compound of the formula

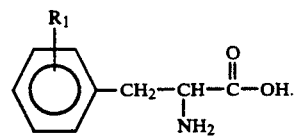

with an acylating compound containing the $R_2$-CO-group to obtain a compound of formula IV.

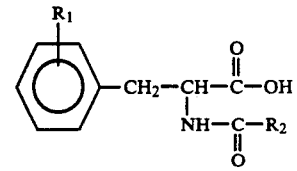

The compound of formula IV may be reacted with a compound containing a group $R_3$ which may be cleaved and replaced by an antibody radical.

The present invention also provides a pharmacological composition comprising a compound of formula I above wherein $R_3$ is an antibody and $R_1$, $R_2$ and $R_{4-7}$ have the meaning given above and a pharmaceutically acceptable diluent.

The compounds of this invention where $R_3$ is an antibody have utility in tumour treatment.

PART A

Melphalan (MEL) is an aromatic alkylating agent which by virtue of its derivation from phenylalanine enters cells by an amino acid transport system. The compounds of this invention are certain derivatives of melphalan prepared with a view to targeting tumour cells.

By acylating the amino group of MEL, an N-acyl derivative was synthesized that was 100 times less toxic than MEL to tumour cells in vitro. An active ester of N-acyl Melphalan (NaM) was then reacted with monolonal antibodies (MoAbs) to the human transferrin receptor (TFR) or the murine Ly-2.1 alloantigen, both of which appear to be internalized. Up to 30 molecules of NaM were specifically bound with retention of alkylating activity and minimal loss in antibody activity. The in vitro cytotoxicity of the conjugate was tested by the inhibition of ($^3$H)-thymidine incorporation into tumour cells which demonstrated the conjugate to be specifically cytotoxic towards antibody reactive cell lines having 10-25 times more activity than free NaM. The conjugate's cytotoxicity was inhibited by free MoAb and unhibited by L-leucine, a competitive inhibitor of MEL uptake. In vivo treatment of mice bearing a murine thymoma with NaM-MoAb conjugates gave prolonged survival times and greater inhibition of growth of established subcutaneous tumours than obtained with NaM, MEL or antibody alone. The in vivo study also indicated that both an intravenous and intratumoral route of administration was more effective than intraperitoneal treatment of subcutaneous tumours.

The preferred procedures used in this invention are detailed below.

Our preferred method involved coupling MoAbs to an N-acyl derivative of MEL via an active ester, thereby specifically guiding the drug into the target cell, whilst reducing any nonspecific toxicity due to contaminating free drug. These drug-Moab conjugates were tested for their coupling efficiency and drug and antibody activities in vitro before progressing to an investigation in several different in vivo models.

MATERIALS AND METHODS

Tumour Cells

BW51470U—(oubain resistant) (9), E3 a clonal variant of the murine thymoma ITT(1)75NS (6,15), and the human cell line CEM (41) were used. The murine cell lines were maintained in vitro in DME, supplemented with 10% heat inactivated newborn calf serum (Flow Laboratories, Australia, 2 mM glutamine (Commonwealth Serum Laboratories. CSL, Melbourne, Australia). The cell line CEM was maintained in RPMI 1640 with the same additives. For in vivo experiments E3 was maintained by serial passage in ascites fluid in (C57BL/6×BALB/c)F$_1$, CBF$_1$) mice, cells from the ascites fluid were washed and centrifuged (1,500 RPM×5 min) twice in DME and phosphate buffered saline (PBS,pH 7.3) resuspended in PBS, and injected subcutaneously (s.c.) or intraperitoneally (i.p.) into CBF$_1$ mice.

Mice

CBA and CBF$_1$ mice were produced in the Department of Pathology, University of Melbourne.

Monoclonal Antibodies

The MoAbs were produced and characterized in the Department: (i) anti-Ly-2.1 reactive with the murine Ly-2.1 specificity (7); and (ii)A3C6 (anti-TFR) reactive with the human transferrin receptor (TFR)(II). The MoAbs were isolated from ascitic fluid by precipitation with 40% ammonium sulphate, dissolution in PBS and dialysis with the same buffer. These crude preparations were either: absorbed onto Protein-A Sepharose (Pharmacia), washed extensively with PBS (pH 7.3) and eluted with 0.2M glycine/HC$_1$ (pH2.8); or passed through an Affigel blue column (Bio-Rad Laboratories, Sydney, Australia) and eluted with PBS. Following neutralisation, MoAbs were dialysed against PBS aliquoted and stored at −70° C. The antibody activity was determined by rosetting with sheep anti-mouse immunoglobulin (SAMG) (12l).

Preparation of N-acetyl Melphalan

A suspension of MEL (200 mg) in dry dimethylformamide (DMF) (1.5 ml) was treated with acetic anhydride (68 microl) and stirred for 1 hr. a further aliquot of acetic anhydride (68 microl) was added for a further 3 hr when a clear solution was obtained. The reaction mixture was then poured into water and extracted with dichloromethane. The dichloromethane extract was washed with water and then dried over anhydrous sodium sulphate. Evaporation of the dichloromethane yielded an oil which was triturated with ether and the resulting solid (62% yield) was recrystallized using dichloromethane/ether. Thin layer chromatography on silica gel plates (DC-Plastik tollien kieselgel 60 F 284, Merck) using chloroform: methanol (2:1) indicated only one spot at Rf=0.35 demonstrating a pure sample.

Preparation and Quantitation of Conjugate

An active ester of NaM was prepared by dissolving 5.0 mg of NaM in 100 microl DMF and N-hydroxysuccinimide (NHS,2.2 mg in 200 microl DMF) added, followed by N,N-dicyclohexylcarbodiimide (3.9 mg in 200 microl DMF). the reaction mixture was allowed to stand at room temperature for 1 hr and for 18 hours at 4° C. and discarded after four weeks if unused. A solution (10–50 microl) of NaM active ester (1.4–7.0 mmpole) in DMF was added to a (0.5–1.0 ml) solution containing 0.5–2.0 mg of affinity purified monoclonal antibody, the mixture was allowed to react for 1 hr at room temperature and any precipitated protein was removed by centrifugation. Free NaM and any other unreacted starting materials were removed by gel filtration chromatography using a Sephadex G-25 column (PD-10; Pharmacia). NaM incorporated in the drug-MoAb conjugates was determined by absorbance spectrophotometry at 258 nm ($E_{258} = 1 \times 10^4 Mp^- cm^{-1}$) after subtracting the protein contribution following its estimation by the Bradford Dye-Binding Assay. The alkylating activity of the conjugate was determined by a modification of the Epstein method. For non-covalent conjugates a (10–50 microl) solution of NaM (1.4–7.0 mmole) in DMF was mixed with MoAb producing a non-covalently associated CBL-MoAb complex which was purified by PD-10 gel filtration.

Antibody Activity

A rosetting assay (12) was used to determine the antibody activity of the drug-antibody conjugates and this was compared to that of antibody which had undergone the same procedures used in the coupling method.

Drug Activity

Two assays were performed to assess drug-activity - these differed in the time the drug-antibody conjugate was in contact with the cells.

(a) 24 hr assay: 100 microl of cells (2–5×10$^6$/ml) were added to a 96 well flat bottom microtitre plate and incubated for 1 hr at 37° C. Free drug (prepared by dissolution 0.5M NaHCO$_3$ and drug-antibody conjugates were filtered through a 0.22 microM millipore filter to ensure sterility and dilutions were performed in sterile PBS; 50 microl of free drug or conjugate were added to the cells using duplicate wells/sample; control wells received 50 microl of medium or PBS and the cells were cultured at 37° C. in a 7% CO$_2$ atmosphere for 24 hr.

(b) 30 min assay: 200 microl of cells (2–5×10$^6$/ml) were collected in sterile plastic centrifuge tubes, resuspended in sterile drug or conjugate and mixed for 30 min at 37° C. The cells were centrifuged (1500 RPM×5 min) and then resuspended in growth medium; 100 microl of cells were then seeded into a microtitre plate using duplicate wells/sample and incubated for 16–24 hr; duplicate samples were performed at each concentration chosen.

Two further assays were devised to demonstrate the specificity of NaM-MoAb conjugates.

(a) Inhibition by free MoAb—as for the 30 min assay (above) excepting that cells were preincubated with free MoAb prior to addition of the conjugate and all steps prior to washing were performed at 4° C.

(b) Inhibition by L-Leucine—as for the 24 hr assay (above), except that cells were incubated in the presence or absence of 1 mM L-leucine over the 24 hr period.

After the incubation period in all the assays 50 microl of medium containing 1 microCi of ($^3$H) thymidine (specific activity=5 Ci/mmol; Amersham) was added and the plates were incubated for 24 hr; cells were then harvested onto a glass fibre filter paper using a cell harvester; dried for 10 min at 80° C. and individual samples separated and counted on a beta scintillation counter. Incorporation of ($^3$H)-thymidine was expressed as a percentage inhibition in incorporation of controls. Standard error for any given point was generated by duplicate determinations and did not exceed 5% for any given experimental point.

In Vivo Experiments:

(a) Survival Study

Tumour cells were injected i.p. into mice and 6 hrs later a series of i.p. treatments began. The percentage of mice in each group was plotted as a function of time.

(b) Tumour Growth (i) Tumour cells were injected s.c. into the abdominal wall of the mouse and allowed to develop into palpable tumours before commencing treatment. Mice were then subjected to a series of i.p. treatments and the size of the tumours measured daily with a caliper square measuring along the perpendicular axes of the tumours; the data was recorded as mean tumour size (product of two diameters±standard error). Experimental groups of 8–10 mice, all of the same sex and age were used in each experiment; or (ii) tumour cells were injected s.c. into the abdominal wall and treatments commenced when palpable tumours had developed; (iii) individual mice were monitored for their respective tumour growth progression; (iv) treatments were administered intratumourallyu (i.t.) and intravenously (i.v.).

Toxicity

For acute toxicity experiments, groups of five CBA mice were given a single injection of various doses of MEL, NaM or NaM-MoAb conjugate. Results were plotted as the % survival of mice against the dose of drug delivered in mg/kg.

RESULTS

These studies were designed to establish the coupling of the N-Acetyl derivative of Melphalan to MoAbs whilst maintaining their drug and antibody activities. Specifically toxic conjugates characterised in vitro were examined for their in vivo inhibitory activity in both serous and solid tumour models.

Coupling of N-Acetyl Melphalan to Antibody the MoAbs, anti-Ly-2.1 and anti-TFR were reacted with different amounts of active ester (Materials and Methods) to produce conjugates which varied in the amount of drug coupled. Up to 30 molecules of NaM could be bound with a good recovery of protein, but when 30–35 molecules were exceeded, precipitation with loss of protein solubility occurred (FIGS. 1,2).

Addition of 70 nmole of NaM active ester to 3 nmole of anti-Ly-2.1 led to an incorporation of 14 molecules of NaM per molecule anti-Y-2.1 with a 70% recovery. By contrast addition of 280 nmole of NaM active ester led to incorporation of 33 molecules with 55% protein recovery. Similar results were obtained when the active ester of NaM was coupled to anti-TFR (FIG. 2). thus the conditions for successful coupling were established—NaM-MoAb conjugates that were further tested in vitro and in vivo had between 10–30 molecules of NaM incorporated per molecule of MoAb. Using the Epstein method to determine the alkylating activity of the NaM conjugates, it was found that >90% of the alkylating activity was retained upon conjugation. Thus, large amounts of NaM could be covalently bound to MoAbs with some loss of protein—however the drug and antibody activity in the conjugates required measurement.

Antibody Activity

The titers of antibody before and after conjugation were measured by the rosetting method (FIG. 3) and were determined as the dilution at which 50% of the E3 and CEM target cells demonstrated rosettes, Anti-Ly-2.1 conjugates containing 10 and 25 molecules of NaM had antibody titers of 1:45,000 and 1:20,000 respectively, whilst the unconjugated anti-Ly-2.1 titer was 1:75,000. Showing better retention of activity, anti-TFR conjugates containing 10 and 30 molecules had titers of 1:60,000 and 1:52,000 respectively whilst the unconjugated anti-TFR titer was 1:75,000 (data not shown). It should be noted that the non-covalent NaM-MoAb conjugates had very similar titers to covalent NaM-MoAb conjugates (data not shown). Thus, there is clearly some loss of antibody activity due to the conjugation procedure, however the titers of the covalently bound antibodies were sufficiently high to enable further experiments.

Cytotoxicity in Vitro

The cytotoxicity of both anti-Ly-2.1 and anti-TFR conjugates were tested on Ly-2+ E3 and TFR+ CEM cells respectively and compared with that of free NaM or NaM non-covalently bound to the antibody concerned. It was clear in both cases that the cytotoxic activity of the covalently bound drug was considerably increased over that of free NaM and less cytotoxic than free MEL (FIG. 4,5). For example, the 50% inhibition in ($^3$H) thymidine incorporation occurred at $9.5 \times 10^{-6}$M for the anti-TFR conjugate compared to $2.5 \times 10^{-4}$M for free NaM (a 25 fold increase in activity) and $3.1 \times 10^{-6}$M for free MEL (a 3 fold decrease in activity) (FIG. 5). In parallel, the 50% inhibition in ($^3$H) thymidine incorporation occurred at $7.5 \times 10^{-6}$M for the anti-Ly-2.1 conjugate compared to $7.5 \times 10^{-5}$ for free NaM, i.e. a 10 fold increase in activity when NaM was specifically targeted to the E3 cell (FIG. 4). By contrast in both experiments, non-covalently associated drug and antibody demonstrated minimal inhibition in ($^3$H) thymidine incorporation (FIG. 4,5). It should be noted that as previously reported (11,15) these MoAbs have no in vitro cytotoxic action on target cells in the absence of complement.

Specific Cytotoxicity

It was necessary to show that the inhibitory effect on target cells was specific. Four procedures were performed.

(a) The 30 min assay was designed to demonstrate that conjugates were cytotoxic as a result of specifically binding target cells at the antigen binding site. Antibody reactive and non-reactive cell lines were employed here: the anti-Ly-2.1 conjugate was shown to bind the antibody reactive cell line, E3, and exerts its cytotoxicity on these cells after 30 min exposure (FIG. 6). In this case 50% inhibition in ($^3$H)-thymidine incorporation occurred at $3.2 \times 10^{-5}$M compared with $3.0 \times 10^{-4}$ for free NaM. To determine whether this inhibition was due to specific binding of the antibody, the Ly-2$^-$cell line, BW51470U$^-$ was used. The BW51470U$^-$ cell line was three times more sensitive to NaM than E3, however comparatively the anti-Ly-2.1 conjugate demonstrated minimal inhibition of the Ly-2$^-$ BW51470U$^-$ cell line.

This assay was also performed for the anti-TFR conjugate against both the TFR$^+$ CEM and TFR$^-$E3 cell lines (FIG. 7) the anti-TFR conjugate brought about 50% inhibition in ($^3$H) thymidine incorporation into CEM cells at a concentration of $5.0 \times 10^{-5}$M compared with $3.0 \times 10^{-4}$M for free NaM. Once again no inhibition of the non reactive E3 cell line was observed in the same molar concentration range.

(b) For both models, an additional experiment was performed using a negative NaM-MoAb conjugate as a non-specific negative control. For example, both anti-Ly-2.1 and anti-TFR conjugates were tested against the Ly-2$^+$ E3 cell line, the anti-TFR conjugate demonstrating no inhibition of the E3 cell line (data not shown). Similarly, the anti-Ly-2.1 conjugate demonstrated no cytotoxicity when tested against the TFR$^+$ CEM cell line (data not shown).

(c) To further ensure that the binding of NaM-MoAb conjugate to target cells was specific and occurred at the antibody binding site, studies were performed to inhibit the binding of conjugate by free antibody at 4° C. At a NaM concentration of $3 \times 10^{-5}$M (15 micro g anti-Ly-2.1)—(10 micro g is saturating) the cytotoxicity of the anti-Ly-2.1 conjugate on E3 target cells was reduced by 80% upon the addition of 100 micro g of anti-Ly-2.1 (FIG. 8). Similarly, the addition of 100 micro g of anti-TFR caused a comparable reduction in the cytotoxicity of the anti-TFR conjugate on CEM target cells (data not shown). This clearly indicates that the cytotoxicity of an NaM-MoAb conjugate is directly related to its antibody binding ability.

(d) MEL is known to undergo active carrier mediated uptake via an amino acid transport system and thus, when incubated with L-leucine, a competitive inhibitor, a 25–40% reduction in cytotoxic activity on CEM cells was observed over the concentration range ($10^{-5}$ to $10^{-4}$M) (FIG. 9). However the same concentration of L-leucine was unable to reduce the cytotoxic action of NaM and NaM-anti-TFR upon CEM cells. This suggests that both NaM and NaM-anti-TFR enter CEM cells by a different mechanism to MEL, the former probably by passive diffusion, and the latter via the TFR receptor.

In Vivo Efficacy

All experiments were performed with E3 variant of the murine thymoma ITT(1) which in vivo is a rapidly proliferating tumour with a doubling time of less than 24 hr.

(a) Survival Study

Groups of 8 CBF$_1$ mice were injected i.p. with $3 \times 10^5$ E3 tumour cells. Four hours after tumour inoculation mice were given one of the following treatments: (i) PBS; (ii) free MEL; (iii) free NaM; (iv) a non covalent conjugate of anti-Ly-2.1 and NaM; and (v)anti-Ly-2.1 conjugate. Each reagent was further administered on day 1 after tumour inoculation, the average amount of NaM or MEL and antibody received per injection was 15 micro g and 150 micro g respectively with one group of anti-Ly-2.1 conjugate treated mice receiving only 7.5 micro g and 75 micro g respectively. It should be noted that anti-Ly-2.1 treated mice received only 75 micro g per injection, this dose is corrected for the fact that anti-Ly-2.1 loses 50% of its activity when conjugated to NaM. The PBS treated mice had a survival time of 25 days whilst that group receiving NaM only died within 30 days of tumour inoculation (FIG. 10). By contrast 90% of the mice treated with 30 micro g of covalently linked NaM-anti-Ly-2.1 and 30% of the mice treated with 15 micro g of conjugate or 30 micro g MEL survived tumour free for more than 100 days. These groups survived significantly longer than mice receiving either non-covalently bound NaM-anti-Ly-2.1 or anti-Ly-2.1 alone—their survival time being only 35 days.

(b) Tumour Growth

Groups of g CBF$_1$ mice injected s.c. with $3 \times 10^6$ E3 tumour cells developed a solid tumour two days after tumour inoculation. These mice were injected i.p. with one of the six treatments described above. The amount of NaM and antibody received per injection was 10 micro g respectively on days 2 and 8 and twice this dose, 20 micro g NaM and 200 micro g antibody, on days 5,6,7 and 9. Once again anti-Ly-2.1 treated mice received half this regimen per injection to allow for its greater activity. There was inhibition of tumour growth in mice which received antibody in their treatments compared to those receiving PBS, MEL or NaM alone. By day 10 the conjugate group had significantly smaller tumours than either the non-covalent NaM-anti-Ly-2.1 conjugate or anti-Ly-2.1 treated mice (FIG. 11). When tracing the individual tumour growth curves of the covalent conjugate treated mice (FIG. 12), no complete regressions were observed, however 25% of the mice demonstrated minor net tumour growth during the treatment period, only increasing in size when no further treatment was administered. It is also clear that one mouse virtually demonstrated no response to the anti-Ly-2.1 conjugate, thereby considerably raising the mean tumour size of this group as whole. It should be noted that an inhibition in tumour growth was observed for all other groups of treated mice compared to those receiving PBS (FIG. 11) suggesting an increased efficacy with earlier treatment. To compare intraperitoneal therapy with other routes of administration a control experiment was designed. 12 groups of 8 CBF$_1$ mice injected s.c. with $2 \times 10^6$ E3 tumour cells developed a solid tumour four days after tumour inoculation. These mice were injected either i.p. or i.v. on days 4 and 6, or i.t. on days 8 and 9 after tumour inoculation with one of either PBS, anti-Ly-2.1, a non-covalent NaM-anti-Ly-2.1 conjugate or the covalent NaM-anti-Ly-2.1 conjugate. The amount of NaM and anti-Ly-2.1 received per injection was 10 micro g and 100 micro g respectively. As previously noted those mice receiving antibody in their treatments had smaller tumours than those receiving PBS alone, independent of the treatment's route of administration (FIG. 13a,b,c). The administration of a total of only 20 micro g of NaM has demonstrated that the efficacy of i.p. conjugate treatment is limited to higher dose therapy as the mice that received Nam-anti-Ly-2.1 conjugate did not have significantly smaller tumours than those receiving either non-covalent NaM-anti-Ly-2.1 conjugate or anti-Y-2.1 along (FIG. 13a.). This is in contrast to the experiment previously described (FIG. 11) in which mice received up to 100 micro g of NaM.

When mice received 20 micro g of these treatments i.v. a significant difference between the efficacy of NaM-anti-Ly-2.1 conjugate and other treatments was observed (FIG. 13b). From days 8-15 the mean tumour size of the conjugate treated group was only approximately 30% of the group receiving PBS alone. This represents a considerable inhibition in tumour growth when one considers that the mean tumour size of mice receiving anti-Ly-2.1 or non-covalent NaM-anti-Ly-2.1 was not significantly lower than that of PBS treated mice over the 8-12 day period.

Mice injected i.t. did not receive their first treatment until the tumours had reached a mean tumour size of 0.65 $cm^2$ (day 8) however by day 11 mice receiving NaM-anti-Ly-2.1 conjugate i.t. had significantly smaller tumours than mice injected i.t. with either PBS, non-covalent NaM-anti-Ly-2.1 or anti-Ly-2.1 alone (FIG. 13c). This trend continued until the termination of the experiment at day 16, whilst the greatest reduction in tumour growth occurred at day 12, the mean tumour size of covalent conjugate treated mice being 61% of that of the PBS treated control mice. It should be noted that mice receiving NaM non-covalently bound to anti-Ly-2.1 did not have smaller tumours than mice receiving anti-Ly-2.1 alone, this suggested that the tumour inhibitory effects of this conjugate were due to the anti-Ly-2.1 component itself.

Toxicity Study

FIG. 14 demonstrates the toxicity of MEL and NaM as reflected in Ld-50 values. As shown the LD-50 of NaM was 115 mg/kg, compared to only 6 mg/kg for MEL, that is MEL is approximately 20 times more toxic than NaM in vivo. NaM-MoAb conjugates were shown to be non-toxic to CBA mice at the maximum tested dose (16 mg/kg).

DISCUSSION

Monoclonal antibodies are capable of exquisite selectivity and thus may appropriately be used to target toxic drugs and unlike the microparticulate carriers, MoAbs can leave the circulation and enter the interstitial fluid and lymph. Although MoAbs can bind with great selectivity to target cells, this may or may not constitute an effective means of drug delivery. A major concern is the degree to which the target antigen is linked to cellular mechanisms for endocytosis and protein sorting, however it appears that the TFR and Ly-2.1 receptors are excellent targets for drug internalization (16). Another problem of the MoAb as a carrier concerns the drug load that can be coupled to the MoAb without denaturation. Previous attempts to couple MEL to antibodies have involved intermediate carriers such as polyglutamic acid, presumably as it is difficult to couple MEL directly to antibodies, however these conjugates appeared ineffective in vivo.

By initially synthesizing a N-acyl derivative of MEL it was possible to make an active ester of this derivative capable of reacting with the epsilon-amino groups of lysines on MoAbs. This NaM active ester was successfully coupled to MoAbs and conjugates of up to 30 molecules of NaM per molecule of MoAb were obtained which retained 50-80% of the neat MoAB activity (FIGS. 1,2). As previously discovered the solubility and antibody activity of conjugates decreased significantly beyond these levels of NaM incorporation.

The NaM-anti-Ly-2.1 and NaM-anti-TFR conjugates were shown to retain the cytotoxic effect of NaM, increasing the anti-tumour activity of bound NaM to 10-25 times respectively that of an equimolar amount of free NaM (FIGS. 4,5). these conjugates also exhibited increased cytotoxicity to target cells in specificity assays performed in vitro. The antibody binding activity of the NaM conjugate clearly resulted in the selective cytotoxicity. This was apparent in the specificity assays in which both NaM-anti-Ly-2.1 and NaM-anti-TFR conjugates displayed cytotoxicity only to Ly-2+ and TFR+ cells respectively, their specific recognition and binding to the target cells making them more potent than NaM alone. The cytotoxic effect the NaM-anti-Ly-2.1 conjugate had on E3 target cells at a particular molar concentration was reduced by 80% on addition of neat anti-Ly-2.1 (FIG. 8), demonstrating that antibody binding is essential for the cytotoxic action of the conjugate. L-leucine, a competitive inhibitor of MEL uptake was unable to protect CEM cells from the cytotoxic action of both NaM and NaM-anti-TFR conjugate (FIG. 9). This suggests that they enter CEM cells by a different mechanism to MEL, the former probably by passive diffusion and the latter via the TFR. Thus is appears that the NaM in the conjugate is directed specifically towards the target cell, and presumably enters the cell via the antigen. It is of interest to note that NaM itself is 100 times less cytotoxic than MEL to CEM cells, yet the NaM-antibody conjugate is only four times less cytotoxic than MEL. It therefore appears feasible that the internalised NaM of the NaM-MoAb conjugate is broken down by the lysosomes to release the more active native molecule, MEL. One should also note that any free or dissociated NaM contaminating the NaM-MoAb conjugate preparation is therefore comparatively non-toxic to the cells in its derivatized form.

Once the efficacy of NaM-anti-Ly-2.1 and NaM-anti-TFR conjugates had been established in vitro, the in vivo activity of the NaM:anti-Ly-2.1 conjugate was investigated in both survival and tumour growth experiments. The survival times of mice inoculated i.p. with the murine E3 tumour clearly demonstrate that NaM covalently bound to anti-Ly-2.1 is a more effective tumour inhibitor than free NaM, NaM non-covalently bound to anti-Ly-2.1 or anti-Ly-2.1 alone (FIG. 10). Although MEL alone enabled 30% of the mice to survive tumour free for >100 days, its use is hindered by its narrow therapeutic range (100 micro g is toxic to a mouse) and thus NaM-anti-Ly-2.1 conjugate treatment is comparatively safer and more efficacious.

Naturally, the site of delivery of both drug and tumour cells must be considered when evaluating these results as it is difficult to see whether specific targeting has in fact been achieved or whether the peritoneal cavity represents nothing more than an elaborate test tube. Consequently, more critical tumour growth systems were also used which determined the ability of these NaM-MoAb conjugates to cross various barriers and localise to tumour cells. In all s.c. tumour growth experiments, therapy did not commence until palpable lumps were established and of the i.p. treatments administered the NaM-anti-Ly-2.1 conjugate was the most effective tumour inhibitor (FIG. 11). It is evident however that even 100 micro g (over 6 injections) of NaM-anti-Ly-2.1 conjugate was unable to drastically inhibit the tumour growth of these mice when the treatment was administered i.p. By contrast when only 20 micro g of NaM-anti-Ly-2.1 was administered i.v. a 70% reduction in the tumour growth of conjugate treated mice was observed (FIG. 13b). This is a dramatic effect considering that when 20 micro g of NaM-anti-2.1 conjugate was administered i.p. using an identical treatment schedule there was only a 35% reduction in tumour growth. It was also apparent that i.v. NaM-anti-Ly-2.1 conjugate treatment was more efficacious than either i.v. non-covalent NaM-anti-ly-2.1 conjugate or anti-Ly-2.1. Treatment of a well established s.c. E3 tumour requires localization and as shown (FIG. 13bl) Nam non covalently bound to anti-Ly-2.1 conjugate is not more effective than anti-Ly-2.1 alone, thus suggesting that the non-covalent association between NaM and anti-Ly-2.1 is insufficiently stable for specific targeting of NaM to the E3 tumour, whereas specific targeting of NaM by the covalent attachment to anti-Ly-2.1 is possible. There is no doubt however that the effectiveness of the covalent NaM-anti-Ly-2.1 conjugate against the s.c. E3 tumour is limited when administered i.p. however i.v. administration appears a more efficacious mode of treatment and currently experiment are being undertaken in which greater doses of NaM-anti-Ly-2.1 conjugate are being administered.

Both i.p. and i.v. therapy may be subject to a number of difficult problems. After administration, the drug may be deactivated by the liver, hydrolyzed in the serum or removed by binding to plasma proteins or by rapid excretion. Moreover, in general, tumours have a relatively poor blood supply and drugs can reach the inner area of the tumour only by diffusion. Thus, although a drug may be a highly selective tumour inhibitor, it may not reach all the tumour cells in a high concentration. For these reasons an experiment was also conducted to determine the effect of i.t. therapy, a route of administration which has given promising results for tumour therapy using immunotixins (18).

The greatest reduction in tumour growth occurred at day 12 when the mean tumour size of covalent NaM-MoAb conjugate treated mice was 61% that of the PBS treated control mice, a significantly greater reduction in tumour growth than observed for mice treated i.t. with non covalent NaM-anti-Ly-2.1 or anti-Ly-2.1 alone (FIG. 13c). In this instance 20 micro g of conjugate administered i.t. does not appear as effective as 20 micro g of conjugate i.v. and only marginally superior to 20 micro g i.p.

REFERENCES PART A

4. Foley, G. E., Lazarus, H., Farber, S., Geren Uzman, B., Boone, B. A. and Mccarthy, R. E. Continuous culture of human lymphoblasts from peripheral blood of a child with acute leukaemia. Cancer 18:52–529,1965.
6. Hogarth, P. M., Edwards, J., McKenzie, I. F. C., Goding, J. W. and Liew, F. Y., Monoclonal antibodies to murine Ly-2.1 cell surface antigen. Immunology 46: 135–144, 1982.
7. Hogarth, P. M. Henning, M. M. and McKenzie, I. F. C. Alloantigenic phenotype of radiation induced thymomas in the mouse. J.Natl. Cancer Inst. 69:619–626, 1982.
9. Hyman, R. and Stallings, V. Complementation patterns of Thy-1 variants and evidence that antigen loss variants "pre-exist" in the parental population. J.Natl.Cancer Inst. 52: 429–436, 1974.
10. Kanellos, J., Pietersz, G. A. and McKenzie, I. F. C. Studies of Methotrexate-monoclonal antibody conjugates for immunotherapy. J. Natl. Cancer Inst. 75:319–332, 1985.
11. Panaccio, M., Thompson, C. H., Zalcberg, J. R. and McKenzie, I. F. C. Monoclonal antibodies to the human transferrin receptor. J.Natl. Canber Inst. (in press), 1985.
12. Parish, C. R. and McKenzie, I. F. C. A sensitive rosetting method for detecting subpopulations of lymphcoytes which react with alloantisera. J. Immunol. Methods 20:173–183, 1978.
13. Pierres, A., Maquet, P., Van Agthovan, A., Bekkhoucha, F., Denizot, F., Mishal, Z., Schmitt-Verhulst, A. and Pierres, M. A rat anti-mouse T4 monoclonal antibody (H129.19) inhibits the proliferation of Ia-reactive T cell clones and delineates two phenotypically distinct (T4+, Lyt-2.3− and T4−, Lyt-2,3+)subsets among anti-la cytolytic T cell clones. J. Immunol. 132: 2775–2782, 1984.
14. Pietersz, G. A., Zalcberg, J. R. and McKenzie, I. F. C. The use of Adriamcycin-monoclonal antibody complexes for specific anti-tumour activity. (unpublished result), 1985.
15. Smyth, M. J. Pietersz, G. A. Classon, B. J. and McKenzie, I. F. C. The specific targeting of chlorambucil to tumours. J. Natl. Cancer Inst. 76: 503–510, 1986.
16. Smyth, M. J., Pietersz, G. A. and McKenzie, I. F. C. The mechanism of action of drug-antibody conjugates. Aust. J. Exp. Biol. Med. Sci. (in press), 1985.
17. Vistica, D. T., Rabon, A. and Rabinovitz, M. Amino acid conferred protection against Melphalan interference with Melphalan therapy by L-Leucine, a competitive substrate for transport. Cancer Letters 6:7–13, 1979.
18. Weil-Hillman, G., Runge, W., Jansen, F. K. and Vallera, D. Cytotoxic effect of anti-Mr 67,000 protein immunotoxins on human tumours in a nude mouse model. Cancer Res. 45: 1328–1336, 1985.

BRIEF DESCRIPTION OF THE DRAWINGS

Figure Legends Part A

Figure legends Part B

Figure 1:
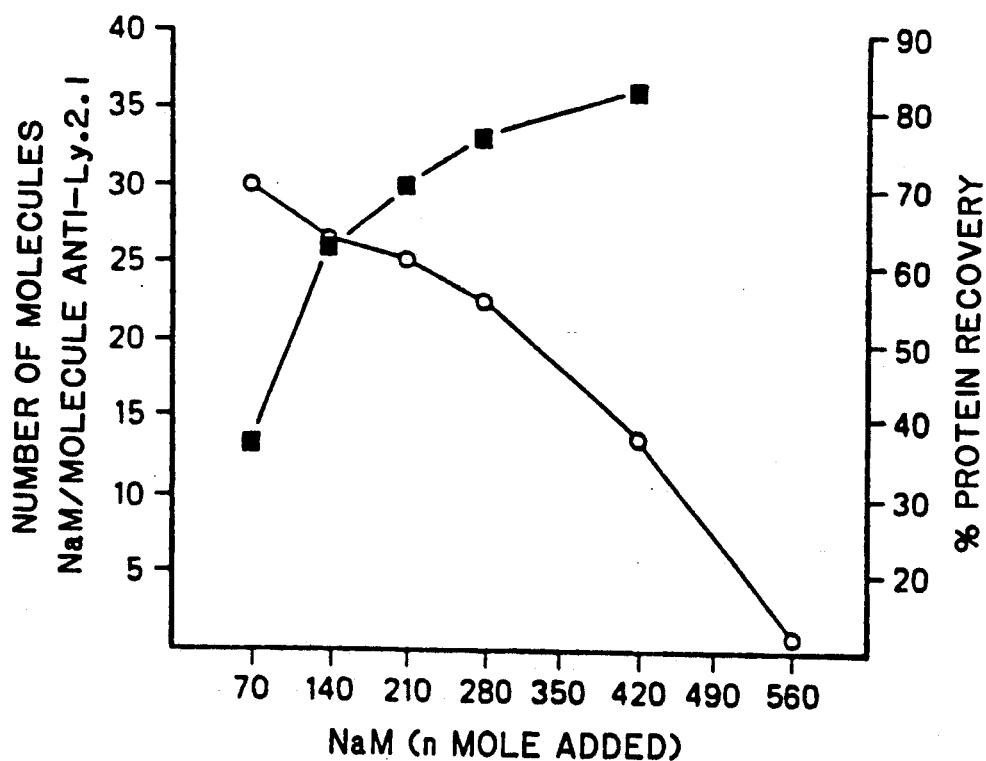
FIG. 1: Coupling of NaM to anti-Ly-2.1 (0.5 mg). Moles of NaM incorporated per molecule anti-Ly-2.1 (■) and protein recovery (o) is shown as a function of the number of n moles of NaM in the reaction mixture (abscisa).
Figure 2:
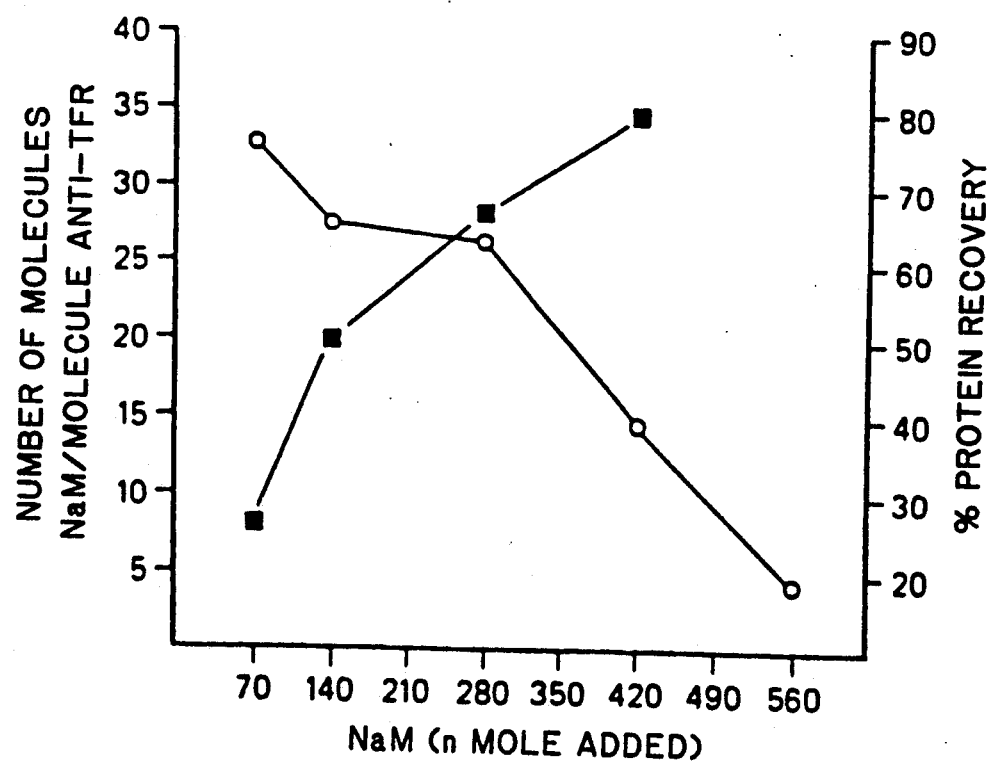
FIG. 2: Coupling of NaM to anti-TFR (0.5 mg). Moles of NaM incorporated per molecule anti-TFR (■) and protein recovery (o) is shown as a function of the number of nmoles of NaM in the reaction mixture (abscissa).
Figure 3:
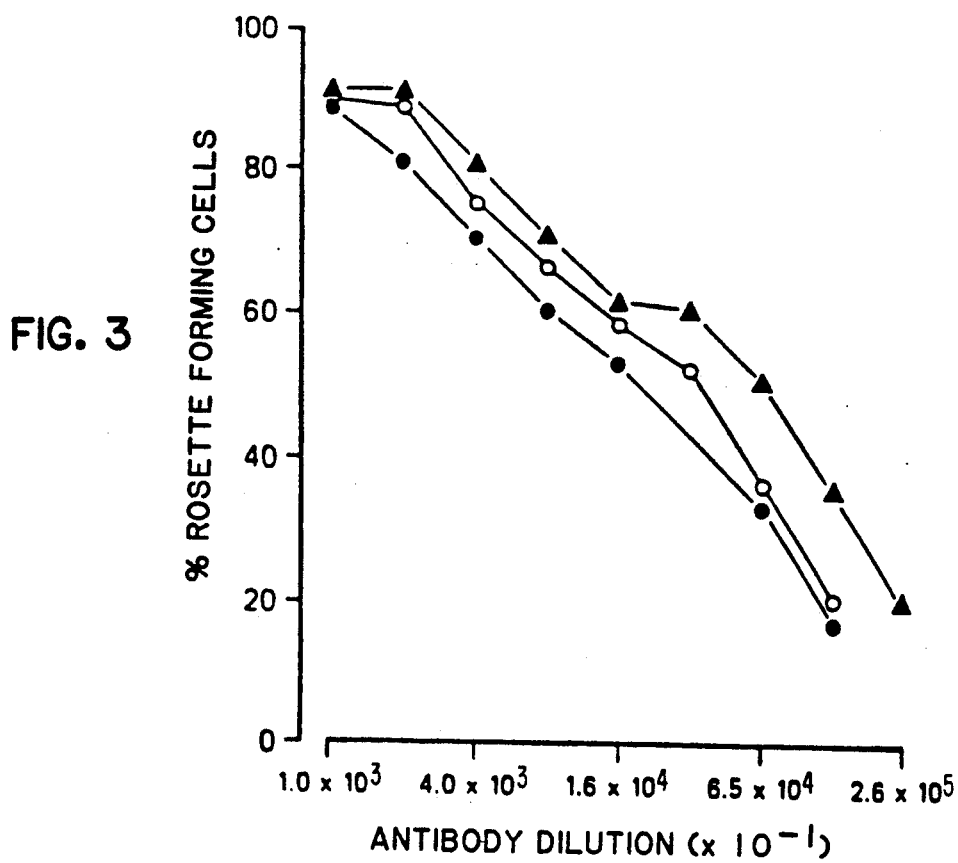
FIG. 3: Antibody titer measured as the % rosette forming cells vs antibody dilution of anti-Ly-2.1 conjugates on ITT(1)75NS E3 target cells. Serial dilutions were performed upon a 0.5 mg/ml solution of either neat anti-Ly-2.1 (▲) and anti-Ly-2.1 with 10 (o) or 25 mol NaM/mol conjugate (●).
Figure 4:
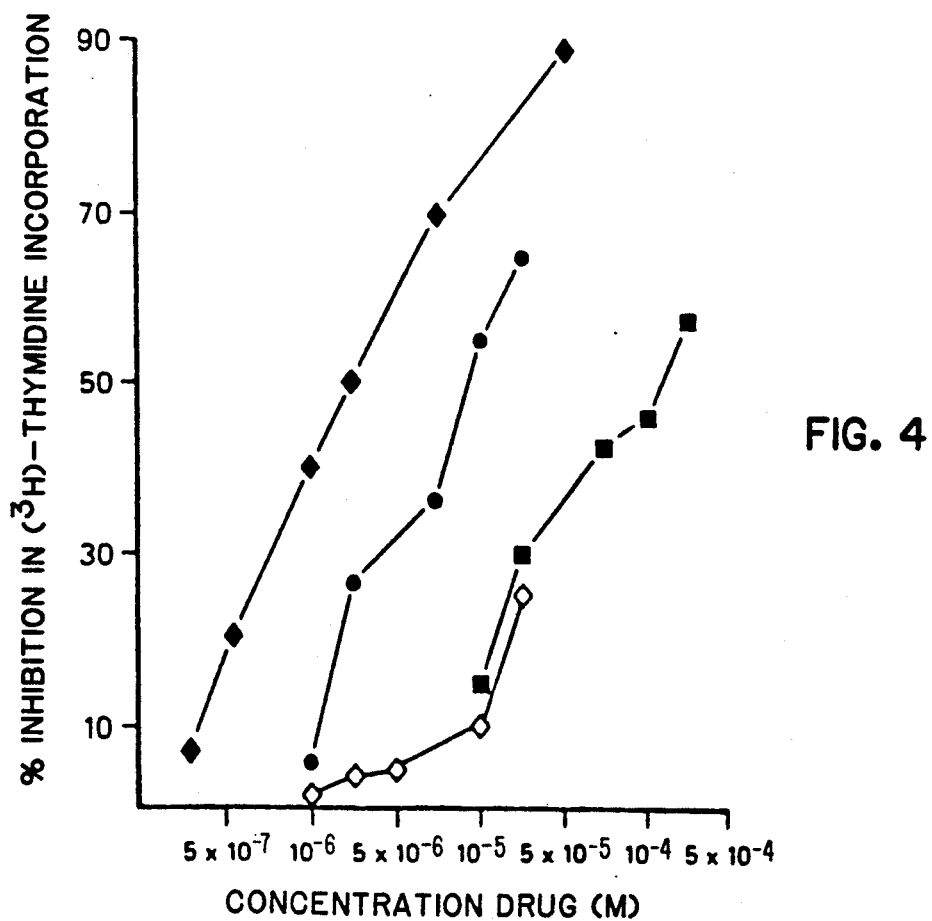
FIG. 4: The inhibitory effect of free NaM (■) NaM non-covalently bound to anti-Ly-2.1 MoAb, 25 mol NaM/mol conjugate (◊), covalently bound to anti-Ly-2.1 MoAb, 25 mol NaM/mol conjugate (●) and free MEL (♦) on ITT(1)75NS E3 cells in a 24 hr assay (see text).
Figure 5:
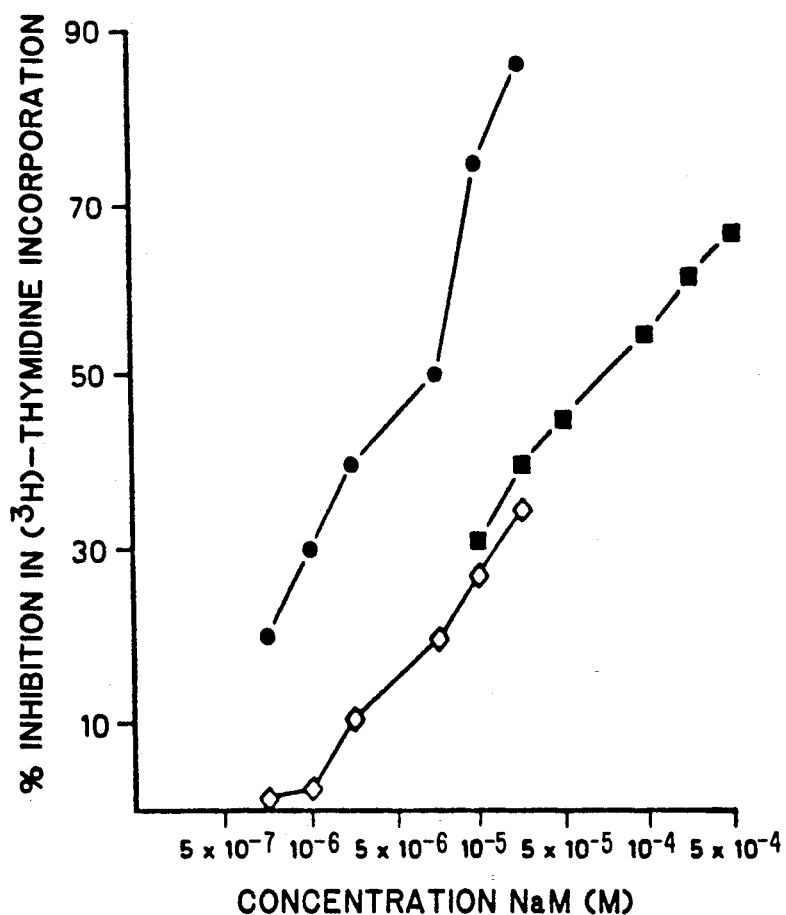
FIG. 5: The inhibitory effect of NaM on CEM cells in a 24 hr assay with the drug either free (■), non-covalently bound to anti-TFR MoAb, 30 mol NaM/mol conjugate (◊) or covalently bound to anti-TFR MoAb, 30 mol NaM/mol conjugate (●).
Figure 6:
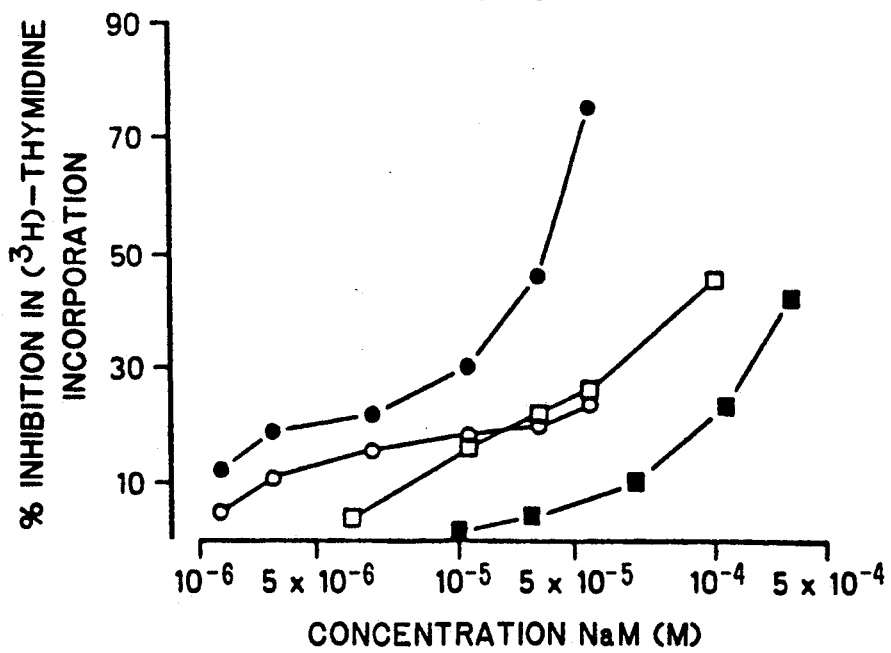
FIG. 6: The inhibitory effect of free NaM (■) of NaM anti-Ly-2.1 conjugate 25 mol Nam/mol conjugate (●) on antibody reactive cells (E3) and free NaM (□) or conjugate (o) on antibody non reactive cells BW51470U⁻ in the 30 min assay.
Figure 7:
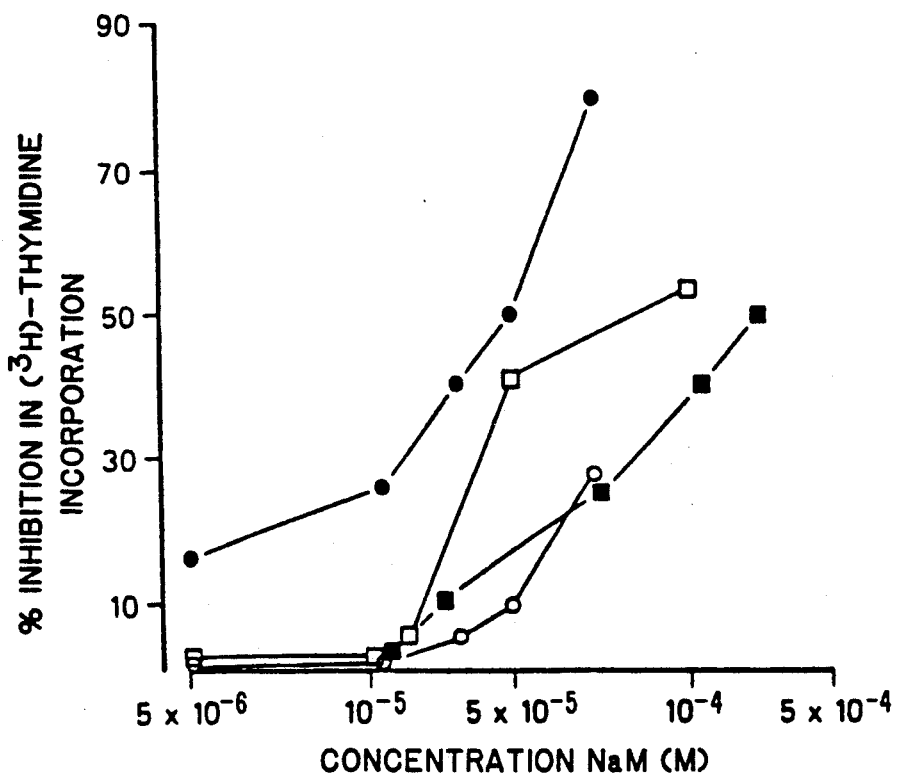
FIG. 7: The inhibitory effect of free NaM (■) or NaM-anti-TFR conjugate, 30 mol NaM/mol conjugate (●) on antibody reactive cells (CEM) and free NaM (□) or conjugate (o) on antibody non-reactive cell E3 in the 30 min assay.
Figure 8:
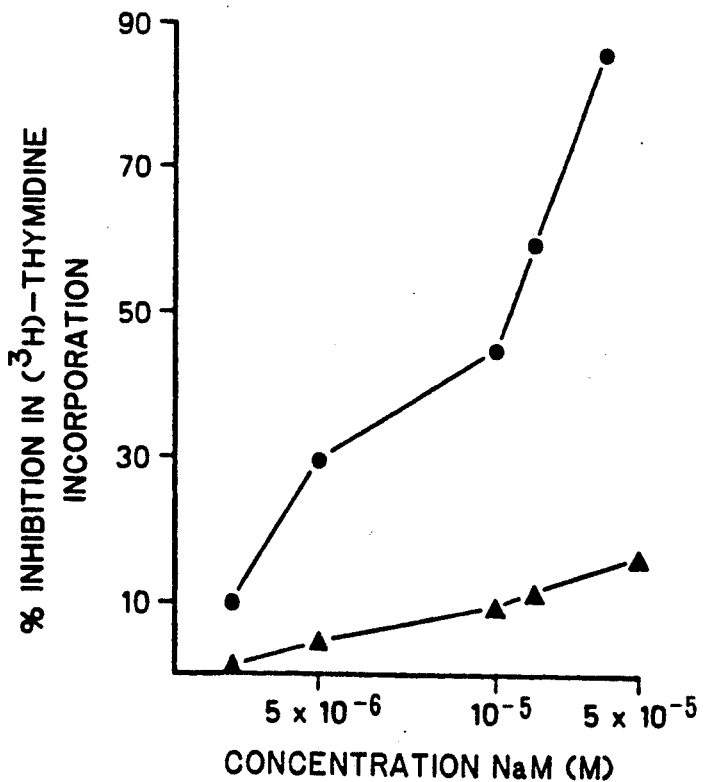
FIG. 8: The inhibitory effect of NaM-anti-Ly-2.1 conjugate, 25 mol NaM/mol conjugate (●) and conjugate plus neat anti-Ly-2.1 (▲) on E3 target cells in the 30 min assay (see text).
Figure 9:
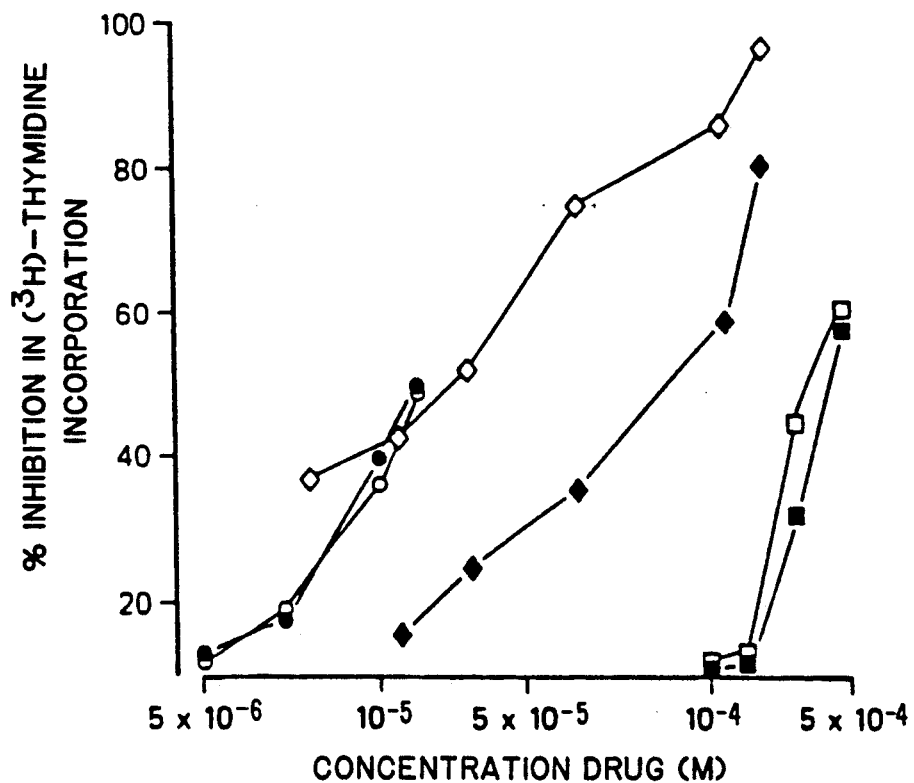
FIG. 9: The effect of L-leucine on the sensitivity of CEM cells to MEL (♦), NaM (■) or NaM-anti-TFR conjugate 30 mol NaM/mol conjugate (●). 1mM L-leucine not present during exposure (o): 1mM L-leucine present (●).
Figure 10:
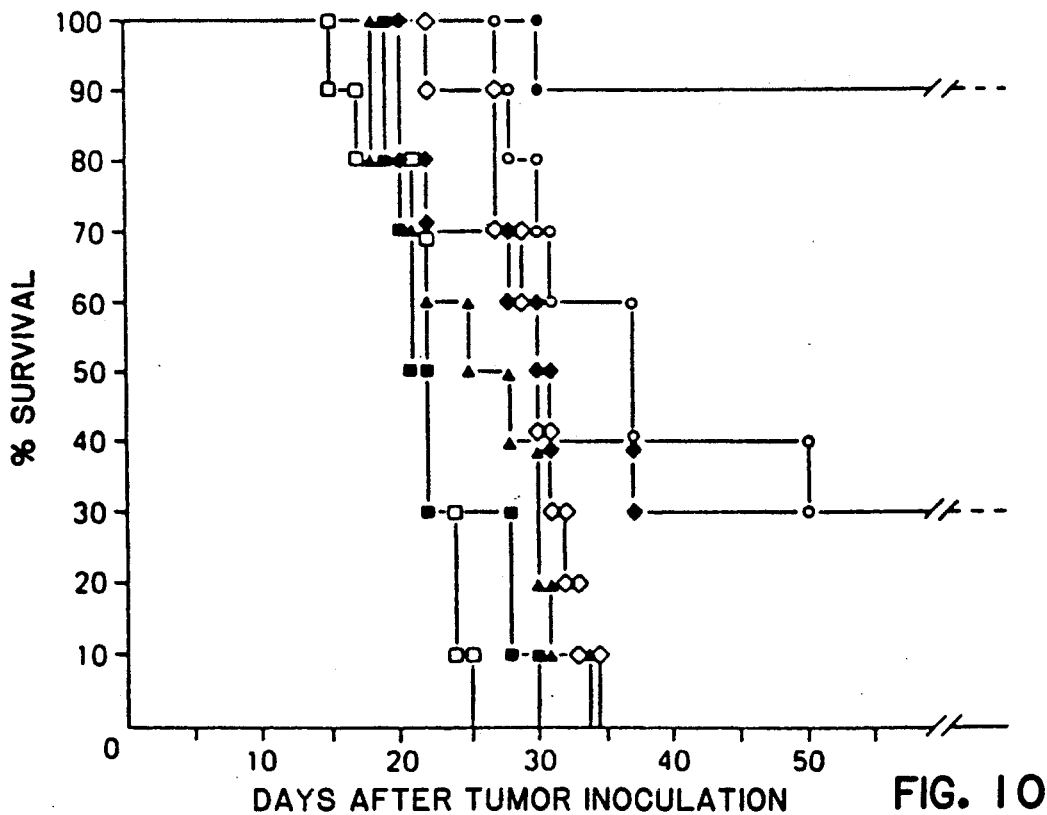
FIG. 10: Survival of CBF₁ mice bearing the ITT(1)75NS E3 tumour. Groups of 8 mice were inoculated with 3×10⁵ cells/mouse; 4 hrs later mice received i.p. either PBS (□), free MEL 30 micro g (♦), free NaM 30 micro g (■), neat anti-Ly-2.1 30 micro g (▲), non-covalent anti-Ly-2.1 and NaM 30 micro g (◊) and NaM-anti-Ly-2.1 conjugate 15 micro g (o) and 30 micro g (●).
Figure 11:
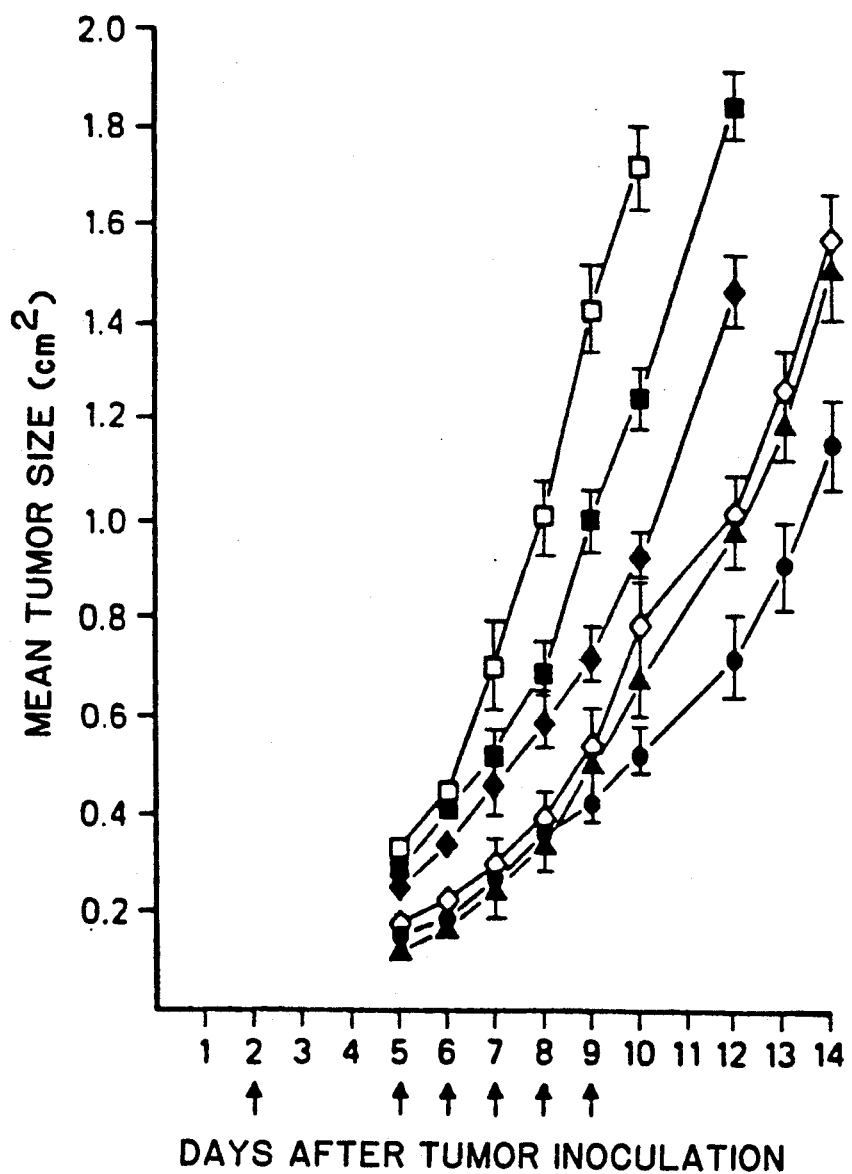
FIG. 11: Growth of the thymoma ITT(1)75NS E3 in CBF₁ mice injected s.c. with 3×10⁶ cells. Groups of 9 mice were given treatments i.p. denoted ( ↑ ): PBS (□), free NaM (■), free MEL (♦), NaM-anti-Ly-2.1 conjugate (●), non-covalently conjugated NaM-anti-Ly-2.1 (◊) and anti-Ly-2.1 (▲). Error bars represent ⁺ standard error from the mean.
Figure 12:
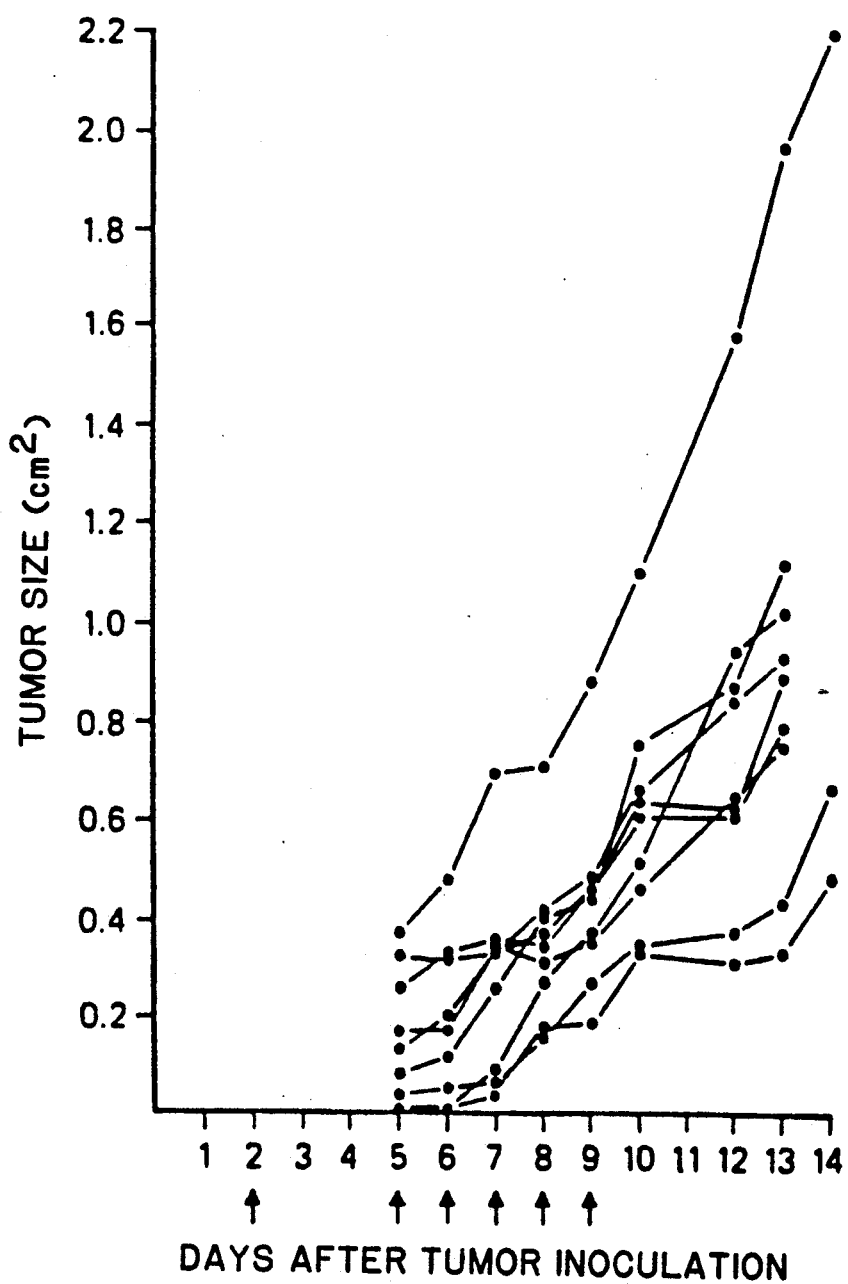
FIG. 12: Individual growth curves of CBF₁ mice injected s.c. with 3×10⁶ ITT(1)75NS E3 tumour cells and treated i.p. on days, 2,5,6,7,8 and 9 with NaM-anti-Ly-2.1 conjugate.
Figure 13:
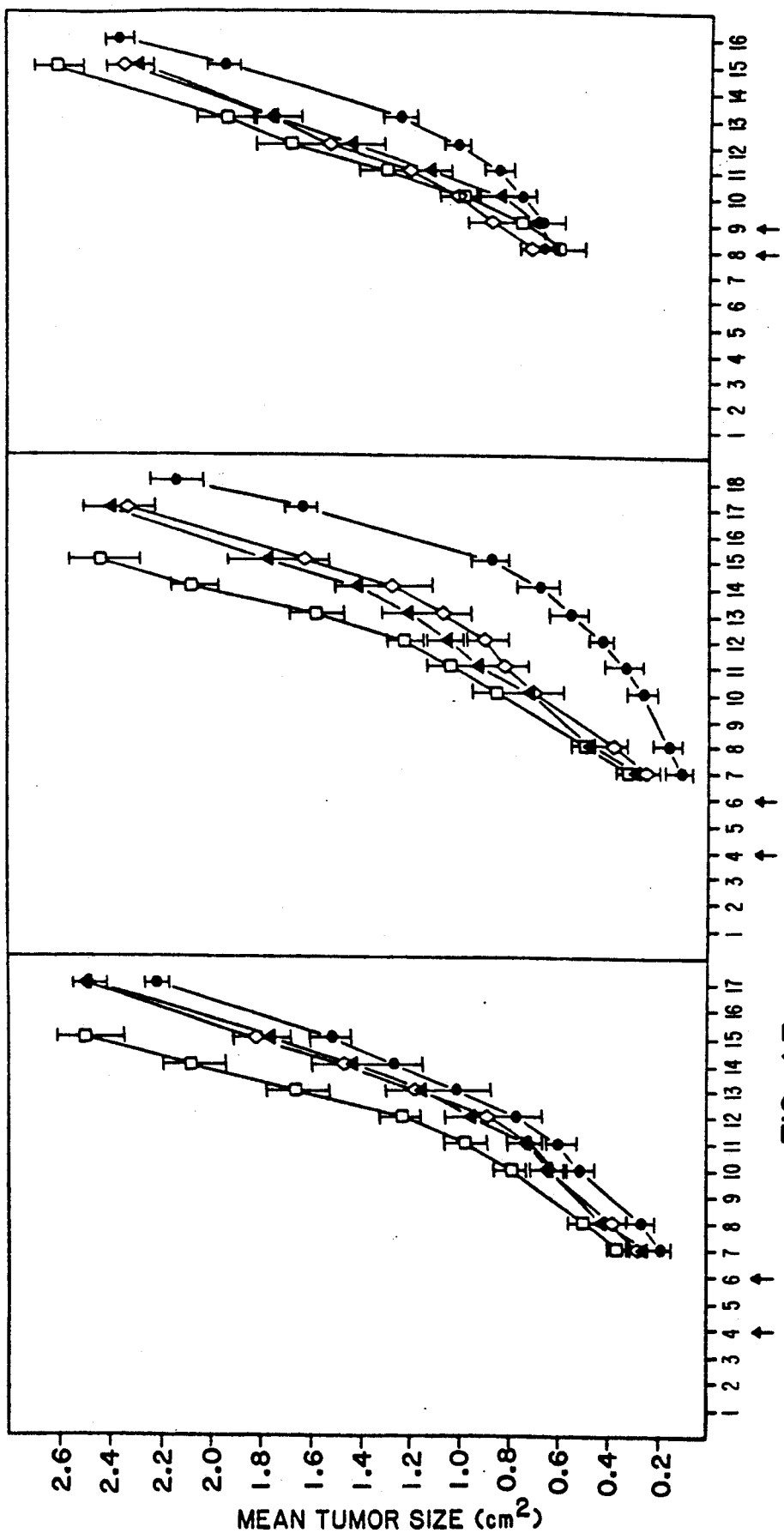
FIG. 13a,b,c: Growth of the thymoma ITT(1)75NS E3 in CBF₁ mice injected s.c. with 2×10⁶ cells. Groups of 8 mice were given the following treatment; (i) PBS (□), (ii) anti Ly-2.1 (▲) (iii) NaM-anti-Ly-2.1 conjugate (●) and non-covalently conjugated NaM-anti-Ly-2.1 (◊) either i.p. (a), i.v. (b) or i.t. (c).
Figure 14:
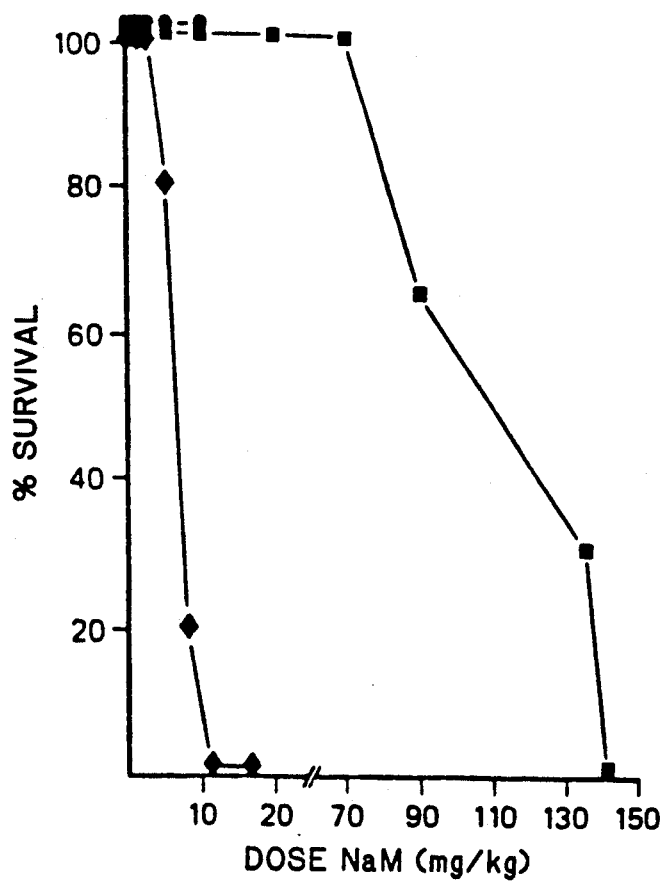
FIG. 14: Toxicity of free NaM (■), free MEL (♦) and NaM-anti-TFR conjugate (●) on non-tumour bearing CBA mice.
Figure 15:
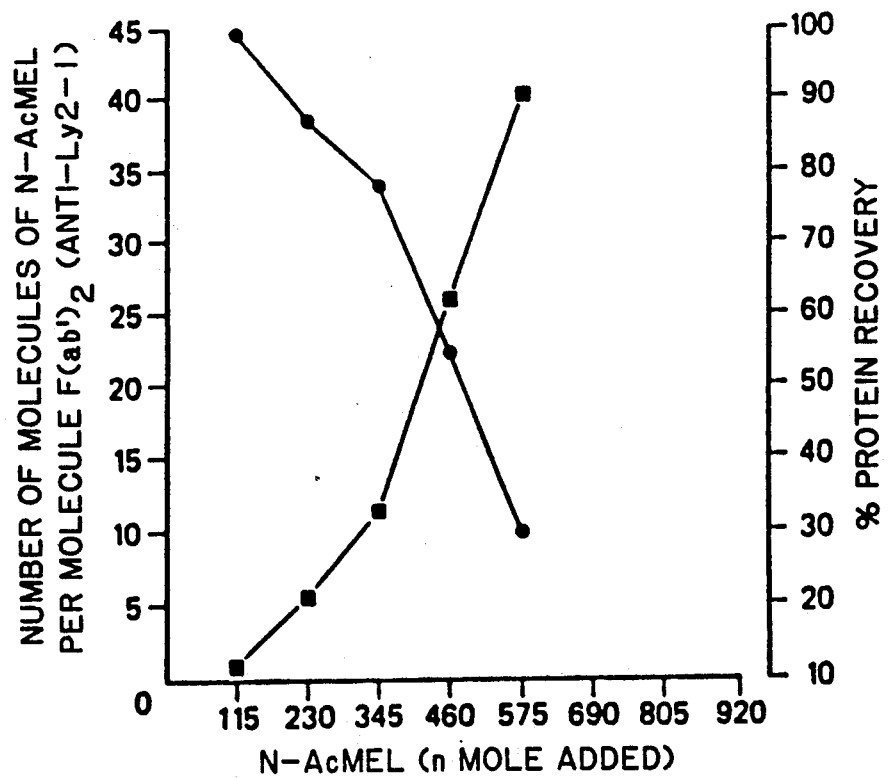

FIG. 15: Coupling of N-AcMEL to anti-Ly-2.1 F(ab')₂ (0.5 mg). Molecules of N-AcMEL incorporated per molecule anti-Ly-2.1 F(ab')₂ (■) and protein recovery (●) is shown as a function of the number of n moles of N-AcMEL in the reaction mixture (abscissa).

Figures 16, 17:
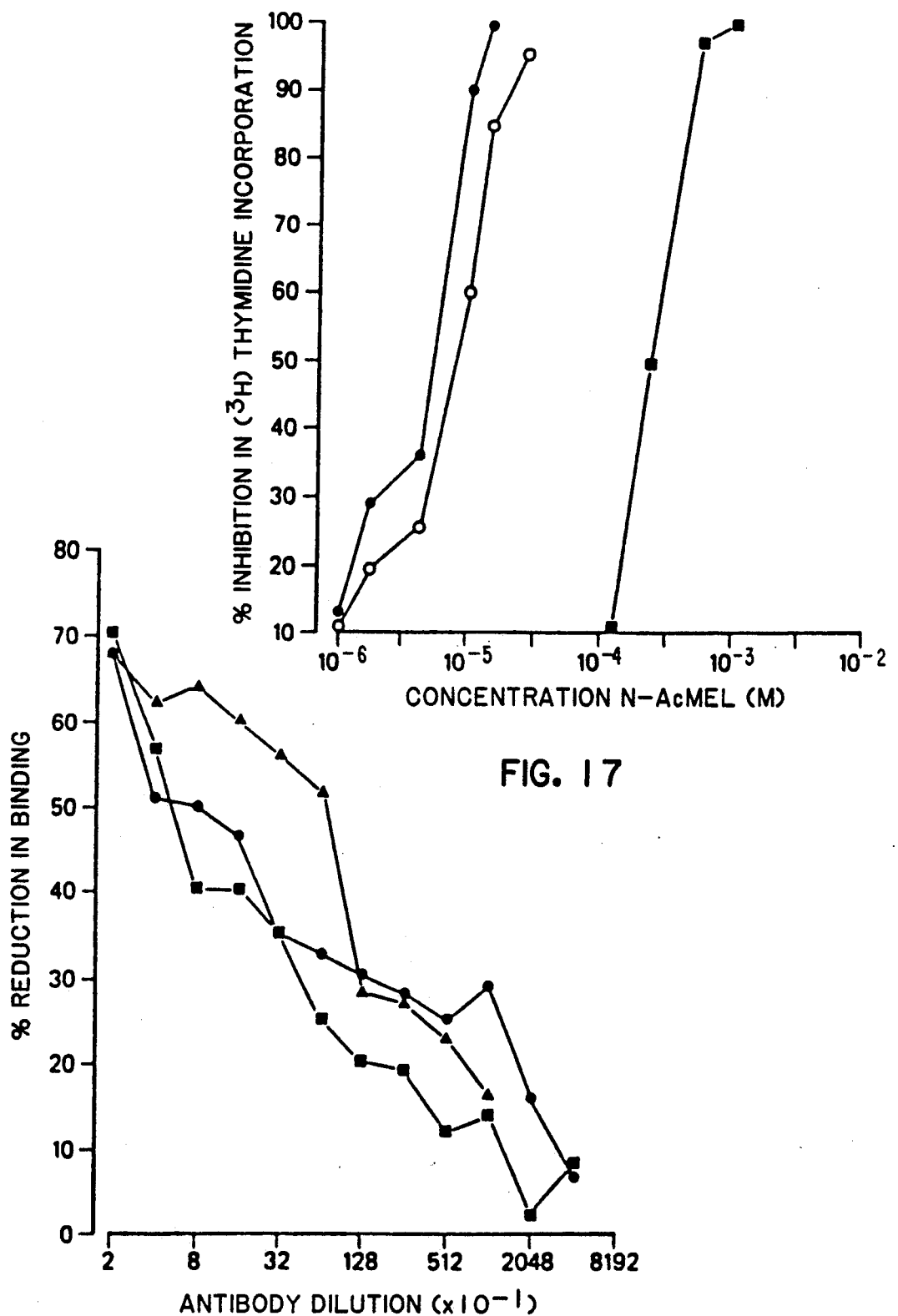

FIG. 16: Antibody titre measured as the percentage reduction in ¹²⁵I-F(ab')₂ binding vs antibody dilution of F(ab')₂ conjugate on ITT(1)75NS E3 target cells. Several dilutions were performed upon a 0.8 mg/ml solution of either anti-Ly-2.1 (▲), anti-Ly-2.1 F(ab')₂ (■) or F(ab')₂ conjugate (●) 20 mol N-AcMEL/mol conjugate.

FIG. 17: The inhibitory effect of free N-AcMEL (■), N-AcMEL covalently bound to anti-Ly-2.1 MoAb, 20 mol N-AcMEL/mol conjugate (o) or N-AcMEL covalently bound to F(Ab')₂ MoAb, 20 mol N-AcMEL/mol conjugate (●) on E3 cells in a 24 hr assay (see text).

Figure 18:
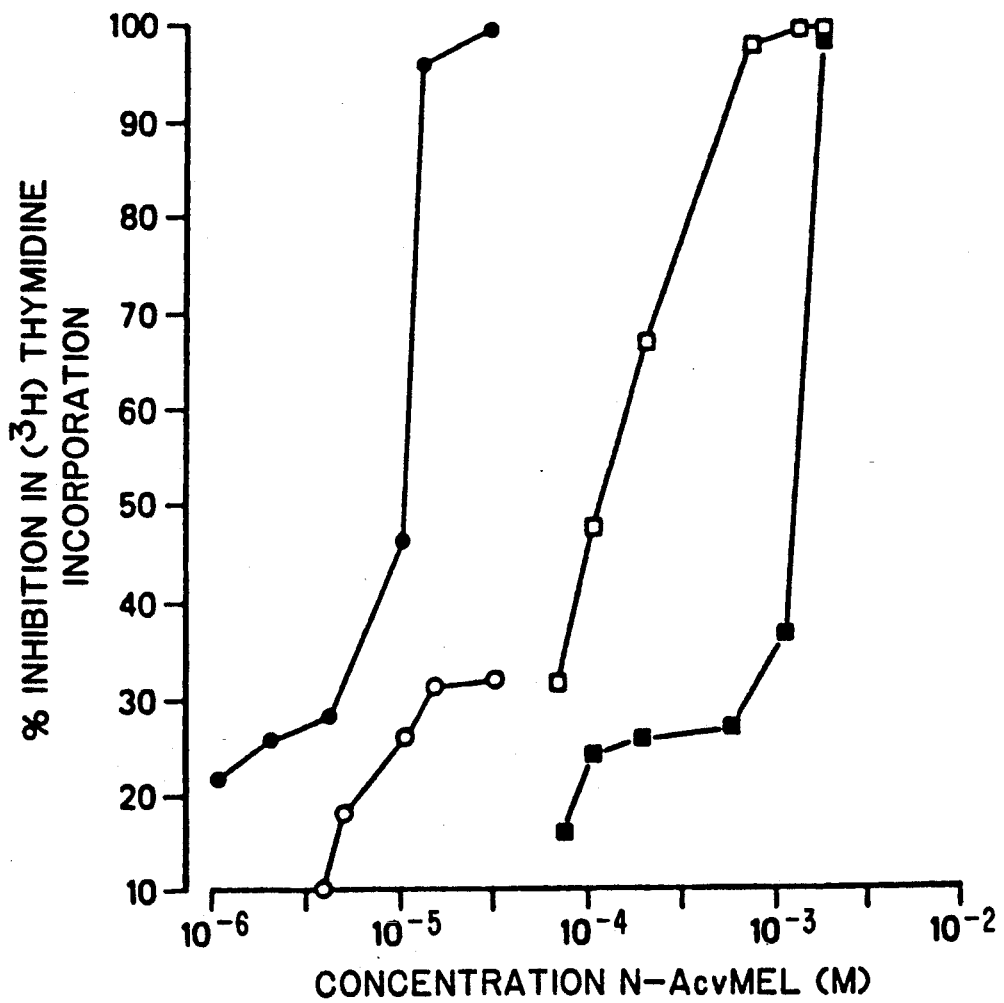

FIG. 18: The inhibitory effect of free N-AcMEL (■) or N-AcMEL-F(ab')₂ conjugate, 20 mol N-AcMEL/mol conjugate (●) on antibody reactive cells (E3) and free N-AcMEL (□) or conjugate (○) on antibody non-reactive cells (EL4) in the 30 min assay.

Figure 19:
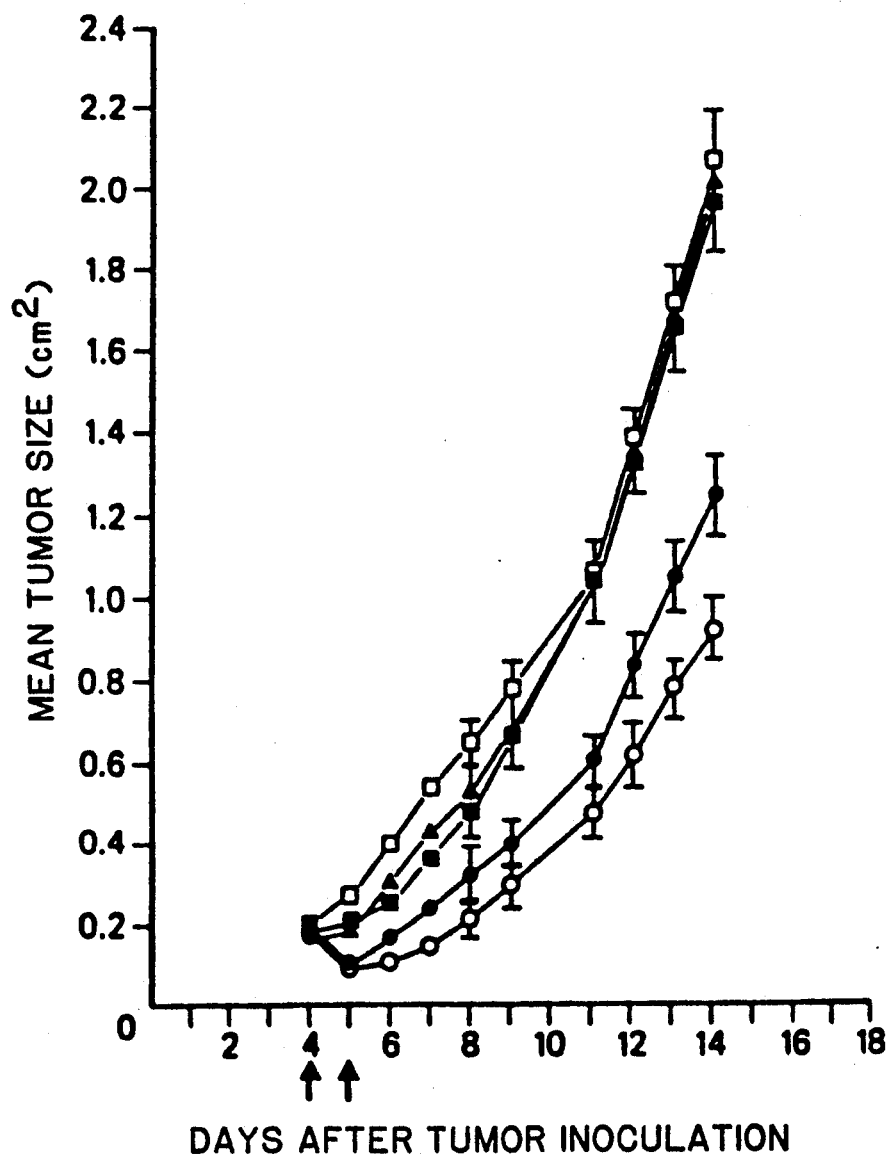

FIG. 19: Growth of the thymoma ITT(1)75NS E3 is CBF₁ mice injected s.c. with 3×10⁶ cells. Groups of 10 mice were given treatments i.v. denoted ( ↑ ); PBS (□), free N-AcMEL (■) N-AcMEL-anti-Ly-2.1 conjugate (●), N-AcMEL-F(ab')₂ conjugate (o) and anti-Ly-2.1 F(ab')₂ (▲). Error bars represent ± standard error of the mean tumour size.

Figure 20:
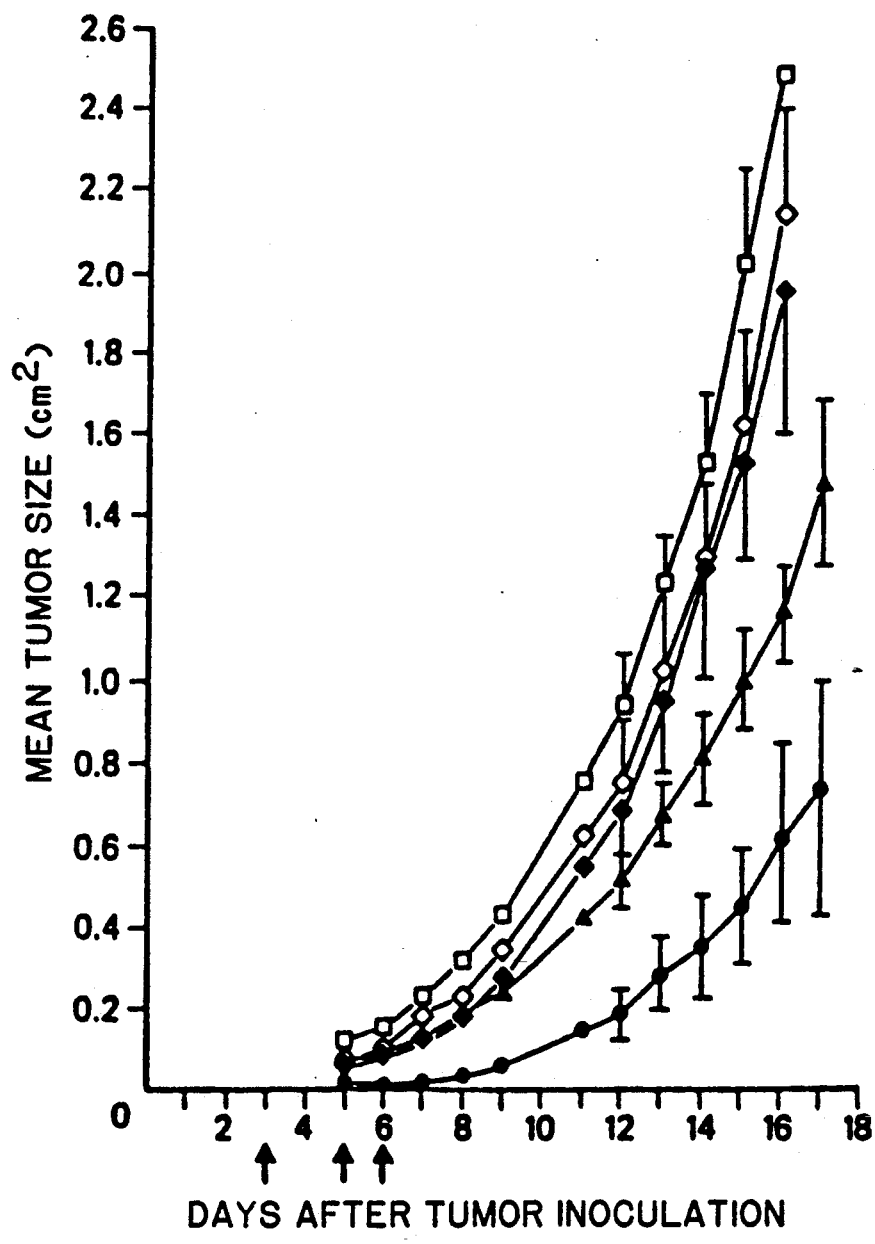

FIG. 20: Growth of the thymoma ITT(1)75NS E3 in CBF₁ mice injected s.c. with 2×10⁶ cells. Groups of 10 mice were given the following treatments i.v. denoted ( ↑ ); PBS (□), free MEL (♦), N-AcMEL-F(ab')₂ conjugate (●), N-AcMEL-anti-TFR conjugate (◊) and anti-Ly-2.1 (▲). Error bars represent ± standard error of the mean tumour size.

Figure 21:
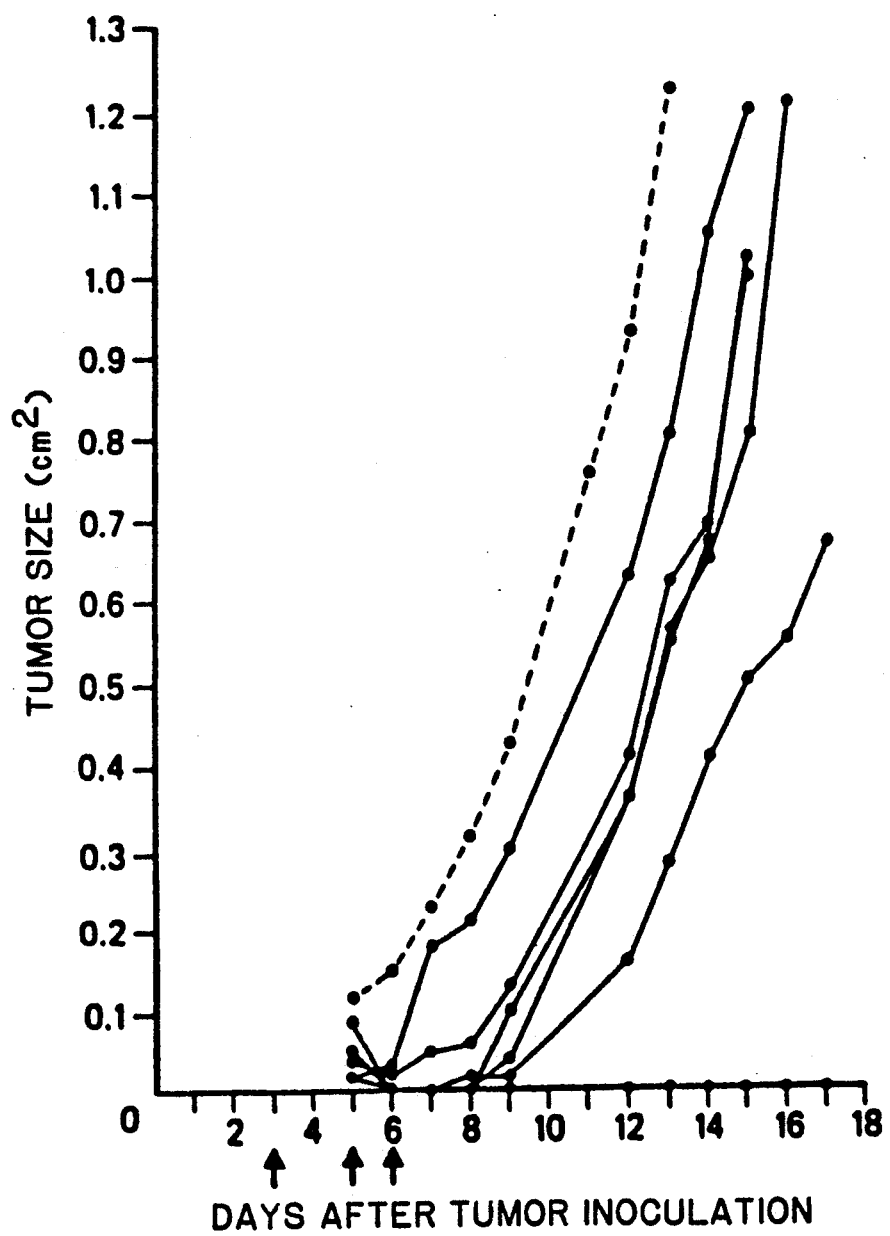

FIG. 21: Individual tumour growth curves of CBF₁ mice injected s.c. with 2×10⁶ ITT(1)75NS E3 tumour cells and treated i.v. (↑) on days 3,5 and 6 with N-AcMEL-F(ab')₂ conjugate. The broken line represents the mean tumour size of PBS treated mice.

PART B

The above N-AcMEL-MoAb conjugates displayed in vitro and in vivo specificity and cytotoxicity however, in an attempt to improve results in vivo we now report on the coupling of F(ab')₂ fragments to N-AcMEL. To increase the accessibility of drug-antibody complexes to tumours and to decrease non-specific binding via Fc receptors N-acetyl-Melphalan (N-AcMEL) was conjugated to F(ab')₂ fragments. These fragments were synthesised by pepsin degradation of IgG MoAb. Up to 20 molecules of N-AcMEL could be successfully coupled to each F(ab')₂ fragment (compared with 25 molecules/intact IgG) with retention of both drug and antibody activity. The N-AcMEL-F(ab')₂ conjugates demonstrated specific cytotoxicity in vitro however despite the absence of non specific Fc receptor binding and greater permeability when using F(ab')₂ fragments, the N-AcMEL-F(ab')₂ and N-AcMEL-IgG conjugates had similar anti-tumour activity in vivo. Conjugates made with whole IgG and F(ab')₂ were equally effective in erradicating subcutaneous solid tumours in mice when injected intravenously. The lower immunogenicity of F(ab')₂ fragments compared with whole IgG and the similar cytotoxicity of their conjugates, suggests that the F(ab')₂ conjugate has greater clinical utility. The use of F(ab')₂ fragments should have several advantages; firstly the non-specific binding to non-tumour cells via Fc receptors would be avoided; secondly the Fc portion is the most immunogenic portion of the Moab so that if the use of murine MoAbs is contemplated for therapy, then the less immunogenic F(ab')₂ preparation could be desirable. Finally the removal of the Fc portion of the MoAb decreases its molecular size by approx. 30%, which has been considered to permit conjugates to more efficiently permeate the physiological barriers and avoid cellular barriers (reticuloendothelial system) when passing from the circulation to a tumour. Subsequently we investigated and compared in the in vitro and in vivo efficacy of F(ab')2 conjugates with conjugates of N-AcMEL and intact IgG MoAb.

MATERIALS AND METHODS PART B

Abbreviations

N-AcMEL = N-acetyl Melphalan
MEL = Melphalan
DME = Dulbecco's Modified Eagles Medium
MoAb(s) = Monoclonal antibody(ies)
TFR = Transferrin receptor
SAMG = Sheep anti-mouse globulin
CBF$_1$ = (C57BL/6×BALB/c)F1
PBS = Phosphate buffered saline

Tumour Cells

E3, a clonal variant of the murine thymoma ITT(1l)75NS (Smyth et al., 1986c); and the murine lymphoma EL4 (Horowitz et al., 1968) were maintained in vitro in DME supplemented with 10% heat inactivated newborn calf serum (Flow Laboratories, Sydney, Australia). 2 mM glutamine (Commonwealth Serum Laboratories, (CSL), Melbourne, Australia), 100 mug/ml Streptomycin (Glaxo, Melbourne, Australia) and 100 I.U/ml penicillin (CSL). For in vivo experiments E3 was maintained by serial passage in the ascites form in (C57BL/6×BALB/c)F1 (CBF$_1$) micel; cells from the ascites fluid were washed and centrifuged (400 g×5 min) twice in DME and phosphate buffered saline (PBS, pH 7.3) resuspended in PBS, and injected subcutaneously (s.c.) into CBF$_1$ mice.

Mice

CBF$_1$ mice were produced in the Department of Pathology, University of Melbourne.

Monoclonal Antibody

The anti-Ly-2.1 MoAb (IgG1) (Hogarth et al., 1982) was isolated from ascitic fluid by precipitation with 40% ammonium sulphate, and the IgG fraction was adsorbed onto Protein A Sepharose (Pharmacia, Piscataway, N.J.), washed extensively with PBS (pH 7.3) and eluted with 0.2M glycine/HCl (pH 2.8). Following neutralisation, the MoAb was dialysed against PBS, aliquoted and stored at −70° C. The antibody activity was determined by rosetting with sheep anti-mouse immunoglobulin (SAMG) Parish et al., 1978).

Preparation of F(ab')2 by Pepsin Degradation

The optimal conditions of degradation adopted for preparation of F(ab')2 fragments of the anti-Ly-2.1 MoAb were 0.1M citrate, pH 3.8, at 37° C. for 6-8 hrs using IgG concentrations of 1 to 2 mg/ml and pepsin concentrations of 25 mug/ml (Parham, 1983). Intact IgG was removed using Protein A-Sepharose (Pharmacia) and each preparation was calculated for yield (>80%) and characterized by polyacrylamide gel electrophoresis under reducing and non-reducing conditions.

Preparation of N-AcMEL-IgG and N-AcMEL-F(ab')2 Conjugates

An N-acetyl derivative of MEL was prepared and conjugated to whole IgG and F(ab')2 as described (Smyth et al., 1986a). Briefly, MEL was acetylated using acetic anhydride and an active ester of this N-AcMEL derivative was then coupled to the amino groups of the MoAb. Antibody Activity: A rosetting assay (Parish et al., 1978) has previously demonstrated the antibody activity of N-AcMEL-IgG conjugates (Smyth et al., 1986a). The antibody activity of N-AcMEL-F(ab')2 conjugates was compared with whole IgG1 and F(ab')2 fragments in a competitive binding assay using radiolabeled $^{125}$I-IgG. In this assay double dilutions were performed using 25 mul antibody, 25 muml F(ab')2 conjugate or 25 muml IgG conjugate in a 96 well round bottom plate and to these 25 mul of $^{125}$I-anti-Ly-2.1 was added; 50 mul of E3 target cells (1.5×10$^6$/ml) were then added and incubated for 30 min before washing (×3) in PBS and cutting the plate and counting individual samples in a gamma counter. It should be noted that control wells did not include 25 mul of "cold" antibody or conjugate and results were calculated as the percentage reduction in $^{125}$I-anti-Ly-2.1 binding of control samples.

Antibody Activity

Two assays measuring the incorporation of [$^3$H] thymidine into tumour cells were performed to assess the drug activity of F(ab')2 conjugates, these differing in the time the conjugate was in contact with the cells a) 24 hr assay: 100 mul of cells (1-5×10$^6$/ml) were added to a 96 well flat bottom microtitre plate and incubated for 1 hr at 37° C. Free drug (prepared by dissolution in 0.5M sodium bicarbonate and N-AcMEL conjugates (F(ab')2 and IgG) were filtered through a 0.22 mum millipore filter to ensure sterility and dilutions were performed in sterile PBS; 50 mul of free drug or N-AcMEL conjugates were added to cells using duplicate wells/sample. Control wells received 50 mul of medium or PBS and the cells were cultured at 37° C. in a 7% CO2 atmosphere for 24 hr, or b) 30 min assay: 200 mul of cells (1-5×10$^6$/ml) were collected in sterile plastic centrifuge tubes, resuspended in sterile drug or F(ab')2 conjugate and mixed for 30 min at 37° C. The cells were centrifuged (400 g×5 min) and then resuspended in growth medium; 100 mul of cells were then seeded into a microtitre plate using duplicate wells/sample and incubated for 1-24 hr. After the incubation period in both assays, 50 mul of medium containing 1 muCi of [$^3$H]-thymidine (specific activity—5 Ci/mmmol; Amersham) was added and the plates incubated for 2-4 hr; cells were then harvested; dried for 10 min at 80° C. and samples counted on a scintillation counter. Incorporation of [$^3$H]-thymidine was expressed as a percentage inhibition in incorporation of controls. Standard error for any given point was generated by duplicate determinations and did not exceed 5% for any given experimental point.

In vivo Experiments a) Tumour Growth

Tumour cells were injected s.c. into the abdominal wall and were allowed to develop into palpable tumours before commencing treatment. Mice were then subjected to a series of intravenous treatments and the size of the tumours measured daily with a caliper square measuring along the perpendicular axes of the tumours; the data was recorded as the mean tumour size (product of two diameters ± standard error). Experimental groups of 8-10 mice, all of the same sex and age were used in each experiment.

RESULTS

These studies were designed to demonstrate that N-AcMEL could be covalently coupled to F(ab')2 fragments of MoAbs whilst maintaining drug and antibody activity in vitro and to compare these conjugates with N-AcMEL covalently bound to IgG MoAb in solid tumour models. Coupling of N-AcMEL to F(ab')$_2$: The anti-Ly-2.1 F(ab')$_2$ was reacted with different amounts of N-AcMEL active ester to produce conjugates which varied in the amount of drug coupled. It was found that the addition of 230 nmole of N-AcMEL active ester to 5 n mole of F(ab')$_2$ led to an incorporation of 6 molecules of N-AcMEL per molecule F(ab')$_2$ with a 85% recovery of protein (FIG. 15). By contrast the addition of twice as much N-AcMEL active ester (460 nmole) led to the incorporation of 25 molecules of N-AcMEL with recovery of 55% of the protein. The conditions for successful coupling had therefore been established and F(ab')$_2$ conjugates that were tested further in vitro and in vivo had between 10–20 molecules of N-AcMEL incorporated per molecule of F(ab')$_2$. It was clear that N-AcMEL could be covalently bound to F(ab')$_2$ fragments with some loss of protein—however the drug and antibody activity of the conjugates required measurement.

Antibody Activity of N-AcMEL-F(ab')$_2$ Conjugates

The titres of antibody before and after degradation and conjugation to N-AcMEL were measured by a competitive radiolabel binding assay (FIG. 18) [i.e. the dilution of cold antibody at which 35% (half the maximum binding observed) of the $^{125}$I-anti-Ly-2.1 binding to E3 target cells was reduced]. F(ab')$_2$ conjugates containing 20 molecules of N-AcMEL had an antibody titre of 1:32, the unconjugated F(ab')$_2$ titre was 1:32 and the anti-Ly-2.1 titre was 1:100. Thus there is clearly some loss of antibody activity upon pepsin degradation to F(ab')$_2$ fragments, however no further measurable loss occurred upon conjugation of up to 20 N-AcMEL molecules. When N-AcMEL incorporation ratios exceeded 20 molecules a significant loss in antibody activity was observed (data not shown).

Cytotoxicity In Vitro

The cytotoxicity of the anti-Ly-2.1 F(ab')$_2$ conjugate was tested on Ly-2+ E3 cells and compared with that of free N-AcMEL and N-AcMEL covalently bound to anti-Ly-2.1. It was clear that the cytotoxic activity of the F(ab')$_2$ conjugate was considerably greater than free N-AcMEL and slightly greater than N-AcMEL-IgG conjugate (FIG. 17). For example, the 50% inhibition in [$^3$H]-thymidine incorporation occurred at a N-AcMEL concentration of $7.5 \times 10^{-6}$M for the F(ab')$_2$ conjugate compared to $4.0'10^{-4}$M for free N-AcMEL and $9.0 \times 10^{-6}$M for N-AcMEL-IgG. Thus F(ab')$_2$ conjugate and IgG conjugate were 40–50 times more cytotoxic then free N-AcMEL.

Specific Cytotoxicity it was necessary to show that the inhibitory activity of N-AcMEL F(ab')$_2$ conjugates was specific for target cells reactive with the MoAb as previously described for N-AcMEL-IgG conjugates (Smyth et al., 1986a). Using the 30 min assay one F(ab')$_2$ conjugate and two cell lines were used. The F(ab')$_2$ conjugate was demonstrated to bind the Ly-2+ E3 cell line and exert its cytotoxicity on these cells after 30 min exposure (FIG. 18). 50% inhibition in [$^3$H]-thymidine incorporation occurred at a N-AcMEL concentration of $1.5 \times 10^{-5}$M compared with $1.5 \times 10^{-3}$M for free N-AcMEL. By contrast EL4 (Ly-2-) which was 10 times more sensitive to free N-AcMEL than E3 was relatively resistant to the cytotoxic effect of the F(ab')$_2$ (Ly-2+) conjugate over the molar concentration range tested.

Tumour Growth

Groups of 10 CBF$_1$ injected s.c. with $3.0 \times 10^6$ E3 tumour cells developed a solid tumour 4 days after tumour inoculation and were injected i.v. with one of the following treatments: (i) PBS; (ii) free N-AcMEL; (iii) F(ab')$_2$;.(iv) a covalent N-AcMEL-IgG conjugate; and (v) a covalent N-AcMEL-F(ab')$_2$ conjugate. Groups received 15 mug of N-AcMEL and/or 150 mug of IgG or F(ab')$_2$ on days 4 and 5. There was inhibition of tumour growth in mice which received either N-AcMEL conjugate, compared to those receiving PBS, N-AcMEL or antibody alone (FIG. 19). By day 6—the conjugate groups had smaller tumours than either the N-AcMel or F(ab')$_2$ treated mice and by day 11 the mean tumour size of N-AcMEL-IgG treated mice was 50% that of PBS treated mice. Even more effective was the F(ab')$_2$ conjugate treatment which had reduced the mean tumour size of that group to 60% of the mean size of the PBS treated group. When monitoring the individual tumour growth curves of the F(ab')$_2$ conjugate treated mice two complete regressions were observed and a further 4/10 of the mice demonstrated a reduction in tumour size during the course of the treatment (data not shown). By day 11 however those tumours that had regressed began to redevelop and grew at half the rate of PBS treated tumours. In order to assess the limitation of N-AcMEL-F(ab')$_2$ and N-AcMEL-IgG treatment using smaller tumour loads and earlier treatment, another experiment was designed in which groups of 10 CBF$_1$ mice were injected s.c. with $2.0 \times 10^6$ E3 tumour cells. These developed a solid tumour 4 days after tumour inoculation. Mice were injected i.v. on days 3, 5 and 6 after tumour inoculation with either PBS, anti-Ly-2.1, MEL, N-AcMEL covalently bound to anti-transferrin MoAb (anti-TFR) (Smyth et al., 1986a1) or N-AcMEL-anti-Ly-2.1 F(ab')$_2$ conjugate. The amount of N-acMEL or MEL administered was 8 mug on day 3, 15 mug on day 5 and 7 mug on day 6 (i.e. total 30 mug N- AcMEL). As previously noted, those mice receiving N-AcMEL and anti-Ly-2.1 in their treatments had smaller tumours than those receiving PBS, MEL or antibody alone (FIG. 20) just seven days after tumour inoculation and by day 11 the mean tumour size of F(ab')$_2$ conjugate treated mice was 15% that of PBS treated mice and 20% that of N-AcMEL-anti-TFR treated mice. The individual tumour growth curves of F(ab')$_2$ conjugate treated mice revealed that 9/10 of the mice demonstrated a reduction in tumour size during the treatment period (days 5–6), 5 of these tumours completely regressing and not redeveloping (FIG. 21). At the termination of F(ab')$_2$ conjugate treatment the remaining 4 tumours began to increase in size, growing at variable rates all slower than the mean growth rate of PBS treated mice. It is also clear that one of the mice only demonstrated a minor response to the F(ab')$_2$ conjugate. In an additional group of mice treated identically with N-AcMEL-IgG (anti-Ly-2.1) conjugate 4/10 of the tumours were completely erradicated (data not shown).

DISCUSSION

To reduce the non-specific toxicity of MEL, a less cytotoxic N-AcMEL derivative was synthesised and coupled to MoAbs (Smyth et al., 1986a). This N-

AcMEL-IgG conjugate was demonstrated to enter cells via the MoAb, not the phenylalanine amino acid transport system and therefore was only cytotoxic to cells which bound the MoAb. In addition N-AcMEL-IgG conjugates more effectively eradicated tumours in vivo than free MEL, N-AcMEL or antibody alone, being most efficacious when administered intravenously (Smyth et al., 1986a). In this study we have attempted to further increase the specificity and cytotoxicity of N-AcMEL-IgG conjugates by cleaving the Fc portion of the MoAb and coupling the derived F(ab')$_2$ fragment to N-AcMEL. Using the same conjugation procedure as for N-AcMEL-IgG conjugates (Smyth et al., 1986a), the N-AcMEL active ester was successfully coupled to F(ab')$_2$ fragments and conjugates with up to 20 molecules of N-AcMEL bound per molecule F(ab')$_2$ were produced (FIG. 15). In addition to retaining its F(ab')$_2$ activity (FIG. 16) the F(ab')$_2$ conjugate was shown to retain the cytotoxic effect of N-AcMEL, increasing the anti-tumour activity of bound N-AcMEL to 50 times that of an equimolar amount of free N-AcMEL (FIG. 17). The F(ab')$_2$ conjugate also exhibited specificity to target cells in cytotoxicity assays performed in vitro (FIG. 18). The F(ab')$_2$ binding activity of the conjugate clearly resulted in the conjugates selective cytotoxicity, as the F(ab')$_2$ conjugate displayed cytotoxicity only to Ly-2+ E3 cells being more cytotoxic than N-AcMEL alone.

These in vitro studies were performed to ascertain whether the F(ab')$_2$ fragments could be covalently coupled to N-AcMEL with retention of the conjugate's specificity and cytotoxicity. The conjugation of F(ab')$_2$ fragments of anti-Ly-2.1 to N-AcMEL has been demonstrated to be comparable to the conjugation of whole anti-Ly-2.1 and N-AcMEL, except that fewer N-AcMEL molecules can be bound to F(ab')$_2$ whilst retaining antibody activity, protein solubility and recovery. Not surprisingly therefore, the F(ab')$_2$ conjugate was as cytotoxic as the intact IgG conjugate in vitro.

Once the cytotoxic activity of the F(ab')$_2$ conjugate had been established in vitro, the in vivo efficacy of the F(ab')$_2$ conjugate was investigated using established solid tumour models. In the first subcutaneous tumour growth experiment, therapy did not commence until palpable lumps were established and of the i.v. treatments administered the F(ab')$_2$ conjugate was the most effective tumour inhibitor (FIG. 19). Its effect was only marginally superior to N-AcMEL-IgG treatment and all of the F(ab')$_2$ conjugate treated mice that demonstrated a reduction in tumour size (6/10) only two mice had tumours that completely regressed, these too redeveloping 6 days after the completion of treatment. In order to assess the limitation of conjugate therapy considering the promising anti-tumour activity of i.v. conjugate treatment in individual mice, we injected CBF$_1$ mice s.c. with $2.0 \times 10^6$ cells and began i.v. treatments one day prior to solid tumour development. Although in this and the initial tumour growth experiment, conjugate treated mice received 30 mug of N-AcMEL, a greater reduction in tumour size was achieved with earlier treatment. Individual tumour growth curves demonstrated that 9/10 of the tumours reduced in size during the course of treatment (FIG. 21) and five of these tumours regressed and did not reappear (>200 days), a result which represents our first successful i.v. cure of subcutaneously implanted ITT(1)75NS E3 tumours using the intravenous route of administration. Earlier i.v. treatment of mice with 30 mug of N-AcMEL-IgG was almost as effective as F(ab')$_2$ conjugate treatment and thus by varying tumour cell number and treatment schedule in two tumour growth experiments we have been unable to demonstrate a major difference in the in vivo efficacy of the N-AcMEL-IgG conjugate and the F(ab')$_2$ conjugate. An important feature of F(ab')$_2$ fragments is their inability to bind Fc receptors on macrophages and hepatocytes which should therefore limit conjugate accumulation in liver and the reticuloendothelial system and on account of their smaller size, F(ab')$_2$ conjugates should also be capable of penetrating the capillary network of the tumour. In contrast however, the shorter half life (faster clearance) and generally lower affinity of F(ab')$_2$ fragments may result in a lower concentration of F(ab')$_2$ conjugate in the tumour than possible with intact IgG conjugate (Wahl et al., 1983). Additionally, it is evident that kinetics of MoAb uptake, the relationship between tumour size and MoAb binding and the site of MoAb deposition are valuable criteria in determining the relative effectiveness of F(ab')$_2$ and intact MoAb-drug conjugates. Consequently, the possibility of using F(ab')$_2$ conjugates therapeutically will depend on giving doses high enough to compensate for their rapid clearance from the tumour site.

REFERENCES PART B

Hogarth, P. M., Edwards, J., McKenzie, I. F. C., Goding, J. W. and Liew, F. Y.: (1982) Monoclonal Antibodies to Murine Ly-2.1 Cell Surface Antigen. Immunology 46:135-144. Horowitz, B., Madras, B. K., Meister, A., Old, L. S., Boyse, E. A. and Stockert, E.: (1968) Asparagine Synthetase Activity of Mouse Leukemias. Science 160:533-535. Parham, P. (1983) On the fragmentation of monoclonal IgG1, IgG2a and IgG2b from BALB/c mice. J. Immunology 131:2895-2902. Parish, C. R. and McKenzie, I. F. C.: (1978) A sensitive rosetting method for detecting subpopulations of lymphocytes which react with alloantisera J. Immunol. Methods 20:173-183. Smyth, M. J., Pietersz, G. A. and McKenzie, I. F. C.: (1986a) Selective enhancement of Anti-tumour Activity of N-Acetyl-Melphalan upon conjugation to monoclonal antibodies. Cancer Res. (in press). Smyth, M. J., Pietersz, G. A. and McKenzie, I. F. C.: (1986b) The mode of action of Methotrexate-monoclonal antibody conjugates. Aust. J. Exp. Biol. Med. Sci. Smyth, M. J., Pietersz, G. A., Classon, B. J. and McKenzie, I. F. C.: (1986c) The specific targeting of chlorambucil to tumours. J. Natl. Cancer Inst. 76: 503-510. Stella, V. J. and Himmelstein, K. J.: (1980) Prodrugs and Site Specific Drug Delivery. J. Med. Chem. 23:1275-1282. Wahl, R. L., Parker, C. W. and Philpott, G. W.: (1983) Improved radioimaging and tumour localisation with monoclonal F(ab')$_2$. J. Nucl. Med. 24:316-325.

Modifications and adaptions may be made to the above described without departing from the spirit and scope of this invention which includes every novel feature and combination of features disclosed herein.

We claim:

1. A compound of formula I

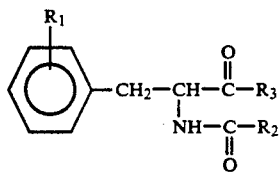

Formula I wherein $R_1$ is of formula II

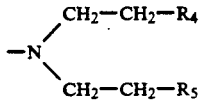

Formula II wherein $R_4$ and $R_5$, which may be the same or different, are bromo, chloro, iodo or alkylsulphonyl; $R_2$ is of formula III

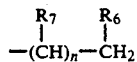

Formula III wherein $R_6$ and $R_7$, which may be the same or different, are H, alkyl, aryl, carboxy, hydroxy or amino and n is 0–10; and $R_3$ is a radical having an antigen binding site.

2. The compound of claim 1, wherein $R_3$ is an antibody, an antibody polymer, an antibody monomer or an antibody fragment having an antigen binding site.

3. The compound of claim 1, wherein $R_3$ is an antibody, an antibody polymer, an antibody monomer or an antibody fragment having an antigen binding site selected from the group showing specificity for one of breast, brain, melanoma, lung, pancreas and colon tumors.

4. The compound of claim 1, wherein $R_3$ is an antibody fragment having an antigen binding site and selected from F(ab')$_2$, F(ab'), IgG$_{2a}$, IgG$_{2b}$, IgG$_1$ and IgG$_3$.

5. The compound of claim 1, wherein $R_6$ and $R_7$ are both H.

6. The compound of claim 5, wherein n=o.

7. A method of making a compound of formula I

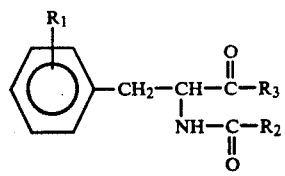

Formula I wherein $R_1$ is of formula II

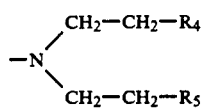

Formula II wherein $R_4$ and $R_5$, which may be the same or different, are bromo, chloro, iodo or alkylsulphonyl; $R_2$ is of formula III

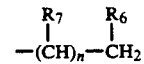

Formula III wherein $R_6$ and $R_7$, which may be the same or different, are H, alkyl, aryl, carboxy, hydroxy or amino and n is 0–10; and $R_3$ is a radical having an antigen binding site, comprising:

acylating a starting compound of the formula

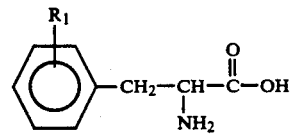

wherein $R_1$ is as defined above, with an acylating compound which contains a $R_2$—CO— group wherein $R_2$ is as defined above, to obtain a compound of the formula IV

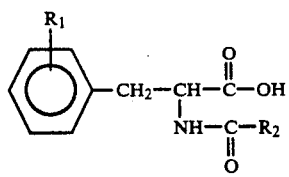

Formula IV wherein $R_1$ and $R_2$ are as defined above, and thereafter reacting the compound of formula IV with a compound having an antigen binding site or reacting the compound of formula IV with a group capable of being cleared and replaced by a radical having an antigen binding site to yield an intermediate compound and then reacting said intermediate compound with a compound having an antigen binding site.

8. The method of claim 7, wherein said starting compound is melphalan.

9. The method of claim 7, wherein the compound having an antigen binding site is an antibody, an antibody polymer, an antibody monomer or an antibody fragment.

10. The method of claim 9, wherein the compound having an antigen binding site is a monoclonal antibody.

11. The method of claim 7, wherein $R_6$ and $R_7$ are both H.

12. The method of claim 11, wherein n=o.

13. The method of claim 7, wherein the carboxylic acid group of the compound of formula IV is converted to an active ester group before it is reacted with a compound having an antigen binding site.

14. The method of claim 13, wherein the compound having an antigen binding site is an antibody, an antibody polymer, an antibody monomer or an antibody fragment.

15. The method of claim 14, wherein the compound having an antigen binding site is a monoclonal antibody.

16. A pharmacological composition comprising a compound of formula I

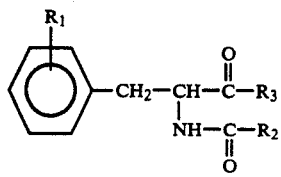

wherein $R_1$ is of formula II

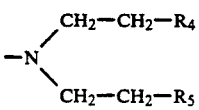 Formula II wherein $R_4$ and $R_5$, which may be the same or different, are bromo, chloro, iodo or alkylsulphonyl;

$R_2$ is of formula III

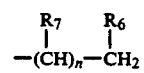 Formula III wherein $R_6$ and $R_7$, which may be the same or different, are H, alkyl, aryl, carboxy, hydroxy or amino and n is 0–10; and $R_3$ is a radical having an antigen binding site together with a pharmaceutically acceptable diluent.

* * * * *